United States Patent
Denina et al.

(10) Patent No.: US 9,327,079 B2
(45) Date of Patent: May 3, 2016

(54) SYRINGE BARREL LUBRICANT COVERAGE QUALITY CONTROL

(71) Applicant: ZebraSci, Inc., Temecula, CA (US)

(72) Inventors: Giovanni Laviste Denina, Moreno Valley, CA (US); Hoang Thanh Nguyen, Riverside, CA (US); Frederick Talley Gertz, Riverside, CA (US); Robert James Schultheis, Temecula, CA (US)

(73) Assignee: ZebraSci, Inc, Temecula, CA (US)

( * ) Notice: Subject to any disclaimer, the term of this patent is extended or adjusted under 35 U.S.C. 154(b) by 0 days.

(21) Appl. No.: 14/632,961

(22) Filed: Feb. 26, 2015

(65) Prior Publication Data

US 2016/0095980 A1    Apr. 7, 2016

Related U.S. Application Data

(60) Provisional application No. 62/060,212, filed on Oct. 6, 2014.

(51) Int. Cl.
| | |
|---|---|
| *G01N 21/00* | (2006.01) |
| *A61M 5/31* | (2006.01) |
| *G01N 21/954* | (2006.01) |

(52) U.S. Cl.
CPC ........... *A61M 5/3129* (2013.01); *G01N 21/954* (2013.01); *A61M 2005/3131* (2013.01); *G01N 2021/9548* (2013.01)

(58) Field of Classification Search
CPC ............. G01N 21/954; G02B 23/2407; G02B 23/2476; A61B 5/1076; G01M 3/38
USPC ...................................................... 356/241.1
See application file for complete search history.

(56) References Cited

U.S. PATENT DOCUMENTS 4,628,969 A * 12/1986 Jurgens, Jr. ............... A61L 2/07
                                                                     134/169 R (Continued)

FOREIGN PATENT DOCUMENTS

| JP | 2006-343138 | 12/2006 |
|---|---|---|
| WO | WO/2013170044 | 11/2013 |
| WO | WO/2014071061 | 5/2014 |

OTHER PUBLICATIONS

Colas et al. Silicones in Pharmaceutical Application. Previously published in Chimie Nouvelle, 15(58), 1779, 1997. http://www.dowcorning.com/content/publishedlit/52-1090-01.pdf (8 pages).
Polin. The Ins and Outs of Prefilled Syringes, A Canon Communications LLC Publication. May 2003, vol. 11, Issue 5 (8 pages).

(Continued)

*Primary Examiner* — Tarifur Chowdhury
*Assistant Examiner* — Md M Rahman
(74) *Attorney, Agent, or Firm* — Lumen Patent Firm

(57) ABSTRACT

A quality control method or system for determining a lubricant coverage at the inside surface of a syringe barrel is provided. The timing for the quality control is not intuitive, yet crucial for patient's safety. The pre-fill test is for a pre-filled (empty or no drug solution), yet oil lubricated, barrel. This pre-fill test needs to be performed within a certain time window immediately following the lubrication. The post-fill test is for a post-filled oil lubricated syringe barrel filled with a solution. This post-fill test needs to be performed after a certain time window has passed from the filling with the solution. The quality control methods could lead to a reduction of health-risks or avoid life-threatening situations associated with syringes that are either below or above the desired lubrication coverage.

6 Claims, 18 Drawing Sheets

(56) References Cited

U.S. PATENT DOCUMENTS

| | | | | |
|---|---|---|---|---|
| 4,718,463 A | * | 1/1988 | Jurgens, Jr. | A61L 2/07 134/169 R |
| 6,067,155 A | | 5/2000 | Ringlien | |
| 6,239,870 B1 | | 5/2001 | Heuft | |
| 2007/0270743 A1 | * | 11/2007 | Ackerman | A61M 5/3243 604/110 |
| 2009/0154789 A1 | * | 6/2009 | Wolfe | G01N 21/958 382/141 |

OTHER PUBLICATIONS

Prefilled Syringes Market (Glass and Plastic)—Global Industry Analysis, Size, Volume, Share, Growth, Trends and Forecast, 2013—2019. http://www.researchandmarkets.com/research/mrs99n/prefilled.

The New Industry Paradigm for Prefilled Success. Issue: Mar. 2013, Posted Date: Mar. 12, 2013.

Chan et al. Syringe Siliconization Process Investigation and Optimization. J Pharm Sci and Tech 2012, 66 136-150.

* cited by examiner

Plastic Syringe Barrel

Plastic Syringe Barrel

Plastic Syringe Barrel

Glass Syringe Barrel

Glass Syringe Barrel

SYRINGE BARREL LUBRICANT COVERAGE QUALITY CONTROL

CROSS-REFERENCE TO RELATED APPLICATIONS

This application claims priority from U.S. Provisional Patent Application 62/060,212 filed Oct. 6, 2014, which is incorporated herein by reference.

FIELD OF THE INVENTION

The invention relates to quality control methods and system for syringe barrels. In particular, the invention relates to quality control of lubricant coverage at the inner surface of a syringe barrel.

BACKGROUND OF THE INVENTION

Syringes already filled with an aqueous-based drug solution play an increasingly important role in the pharmaceutical industry and the medical community. For the purposes of this invention, such filled syringes are defined to as post-filled syringes; i.e., post/after the time of filling the syringe with the solution, which is in contrast to pre-filled, which is defined for the purposes of this invention to as prior/before the time of filling the syringe with the solution.

Within the industry community, post-filled syringes represent a market share of over $2 billion dollars, with over 60 products on the market and a growing number of protein-based products expected to enter the market in the near future.

From a medical standpoint, post-filled syringes allow for improved drug delivery that is less wasteful, safer, and frequently easy enough for patients to do without the oversight of a medical professional.

An important part of the syringe is the plunger system, which relies on a layer of lubricant to allow for ideal glide force and ensuring complete delivery of the drug product.

The most common lubricant is silicone-based oil, and the siliconization of these syringes, understandably has played an important part in the development of pre-filled syringes. As well as providing an ideal glide force and ensuring that the plunger travels the full path, siliconization also provides several advantages. It is a hydrophobic oil allowing for easy emptying of a drug product, and the oil is low reacting, frequently used as a buffer layer between the syringe barrel and the drug product ensuring no reaction takes place between the two materials.

This has led to the use of siliconization in other applications beyond the post-filled syringe market, such as use as coating in vials and ampules in some cases. Siliconization is a widely used process that has been often overlooked and under-championed, despite its use, and manufacturing concerns over proper siliconization and the demands for testing to determine uniform coverage have often gone overlooked. An example of this is the Amgen recall of 2006 in Europe, requiring millions of drug product to be returned as improper siliconization was to blame for improper dosing.

As important as this process is, several manufacturing concerns are still being dealt with to-date. Too much silicone oil can lead to protein aggregation and too little oil can be telling of an improper spraying within the manufacturing environment. Protein aggregation has the potential to produce improper antibodies within the drug that on delivery could cause an unwanted, potentially fatal response in a human. In systems with agitation, the protein build-up is significant enough to be observed visually with the naked eye. Also, large amounts of sprayed oil have led to oil droplets within the drug product.

For sensitive applications, such as injections into the human eye for treatment, silicone oil droplets are observable within patients with an unknown amount of damage. As the FDA and other governing bodies work to not only establish the danger of these and other leachables, it is important to develop technology that will allow the greatest amount of quality control over the manufacturing process. The only way to guarantee high-quality coatings being delivered is through 100%, high-speed inspection of pre-filled and/or post-filled syringes, which is the topic of this invention.

SUMMARY OF THE INVENTION

A quality control method or system is provided for determining a lubricant coverage at the inside surface of a syringe barrel for a pre-filled and post-filled syringe barrel. For the purposes of this invention, post-filled syringes are defined as syringes post/after the time of filling the syringe with the solution, which is in contrast to pre-filled syringes, which are defined for the purposes of this invention to as prior/before the time of filling the syringe with the solution.

For the pre-filled syringe barrel, an un-filled/pre-filled syringe barrel is provided having an inner surface, where the inner surface has not yet been covered with a lubricant. A lubricant is applied to cover to the inner surface of the pre-filled syringe barrel using a lubricant covering device, therewith creating a lubricant-covered pre-filled syringe barrel. Prior to filling the lubricant-covered barrel with an aqueous-based solution, one or more pre-fill optical properties are obtained of the lubricant-covered pre-filled syringe barrel. The pre-fill optical properties are obtained at a time $T_e$ defined as $$T_{e,0} < T_e \leq T_{e,1}$$

where $T_{e,0}$ is the time of the applying the lubricant, where $$T_{e,1} = 0.051\eta$$

defined in minutes, where $\eta$ is a viscosity of the applied lubricant and defined in cSt, and where the pre-fill optical properties are obtain using a first imaging system. A pre-fill quality measure is determined for the lubricant-covered pre-filled syringe barrel using the pre-fill optical properties as input to a computer-implemented pre-fill barrel quality measure determination program executed on a first computer. The pre-fill quality measure is used by a first syringe processing system to reject or accept the lubricant-covered barrel based on a predetermined pre-fill quality threshold.

For the post-filled syringe barrel, a lubricant-covered un-filled/pre-filled syringe barrel is provided, where the lubricant-covered pre-filled syringe barrel has not yet been filled with an aqueous-based solution. The lubricant-covered pre-filled syringe barrel is filled with an aqueous-based solution (e.g., an aqueous-based drug-containing solution) using an aqueous-based solution filling device, therewith creating a lubricant-covered post-filled syringe barrel. One or more post-fill optical properties are obtained of the filled lubricant-covered syringe barrel, where the one or more post-fill optical properties are obtained at a time $T_f$ defined as $$T_f \geq T_{f,1}$$

where $$T_{f,1} = 8.8 \exp(0.0063\eta)$$

defined in minutes and defined from $T_{f,0}$, where η is the viscosity of the applied lubricant and defined in cSt, where $T_{f,0}$ is the time of the filling the aqueous-based solution, and where the post-fill optical properties are obtained using the first imaging system or a second imaging system. A post-fill quality measure is determined for the filled lubricant-covered barrel using the post-fill optical properties as input to a computer-implemented post-fill barrel quality measure determination program executed on the first computer or a second computer. The post-fill quality measure is used by the first syringe processing system or a second syringe processing system to reject or accept the filled lubricant-covered barrel based on a predetermined post-fill quality threshold.

To guarantee or significantly improve high-quality coatings for syringe barrels needs to occur through 100%, high-speed inspection of pre-filled as well as post-filled syringes along the processes specified in this invention. Failure to perform both these quality tests, i.e. at both stages of the processing pipeline, may lead to serious consequences and health issues, which could manifest when poorly or inadequately tested syringes are used on patients.

DETAILED DESCRIPTION

Definitions

Post-filled syringes are defined as syringes post/after the time of filling the syringe with the solution.

Pre-filled syringes are defined to as prior/before the time of filling the syringe with the solution.

The lubrication of a syringe barrel with oil and its distribution plays a vital role in the performance of the syringe since it allows for a reliable and consistent motion of the plunger in the syringe barrel. Since the lubricating oil is transparent, and is applied to a transparent barrel (e.g., plastic or glass), a simple visual inspection of the syringe cannot ensure that there is adequate or any coverage of the lubricant in the syringe.

Figure 1:
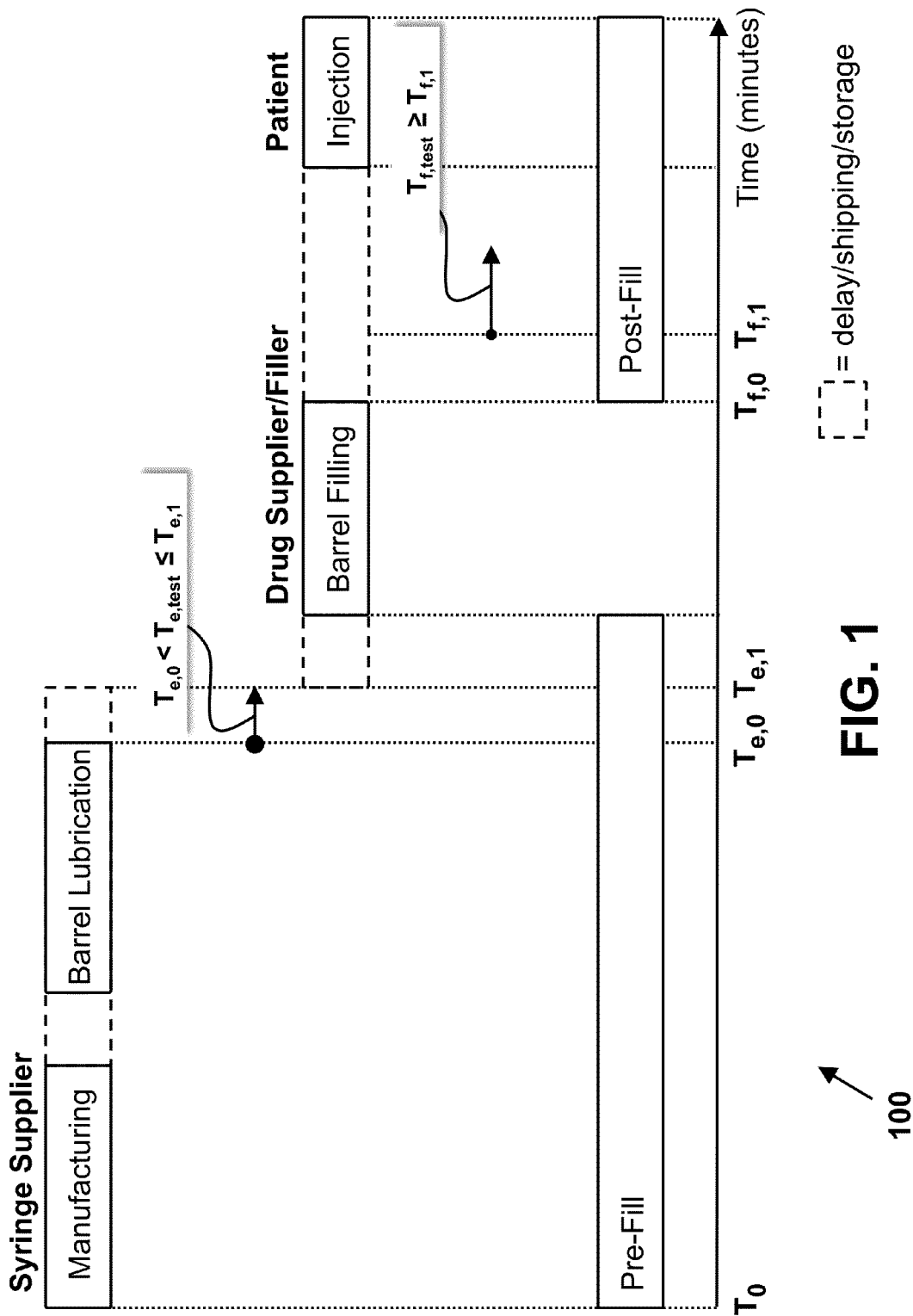
FIG. 1 shows the timing and process 100 of syringe barrel testing in the pre-fill and post-fill stages of the process according to an exemplary embodiment of the invention.

Embodiments of the invention can be used in two separate, yet complimentary scenarios within the pharmaceutical industry (FIG. 1). The first scenario involves the syringe manufacturer/supplier who can use the method immediately following the spraying of the lubricant, while the syringe is still in a pre-fill stage, to inspect the interior surface of the barrel and to verify that it is coated with adequate coverage to ensure good device performance. The timing for inspection ($T_{e,test}$) for adequate (pre-fill) coverage is not intuitive, yet crucial for the quality control and further handling of the syringe.

The second scenario involves the drug-supplier/filler side of the industry. While drug manufacturers order syringes and insist that they have been inspected for lubricating oil coverage, the dynamic nature of a thin-film liquid lubricant coating can allow for migration, especially in an uncontrolled shipping environment where temperatures can vary. Due to these issues it is of utmost importance for drug manufacturers/fillers to inspect the distribution of the lubricating oil. Incoming samples should be inspected immediately after being received to guarantee good performance of the product. Since empty (pre-filled) syringes may be stored with the drug manufacturer in excess of months, it is important that the syringe be inspected again after being filled with an aqueous-based solution so as to provide a safe, reliable product to the consumer. The timing for this inspection ($T_{f,test}$) for adequate (post-fill) coverage upon filling the syringe with an aqueous-based solution is not intuitive, yet crucial for the quality control and further handling of the syringe.

Implementing the inspection processes embodied in this invention at both the suppliers and the drug manufacturer's facilities will guarantee that a high-quality, reliable product will be provided to the consumer, without or at least a significant reduction of oil lubrication problems.

Barrel Lubrication

Figures 2, 3:
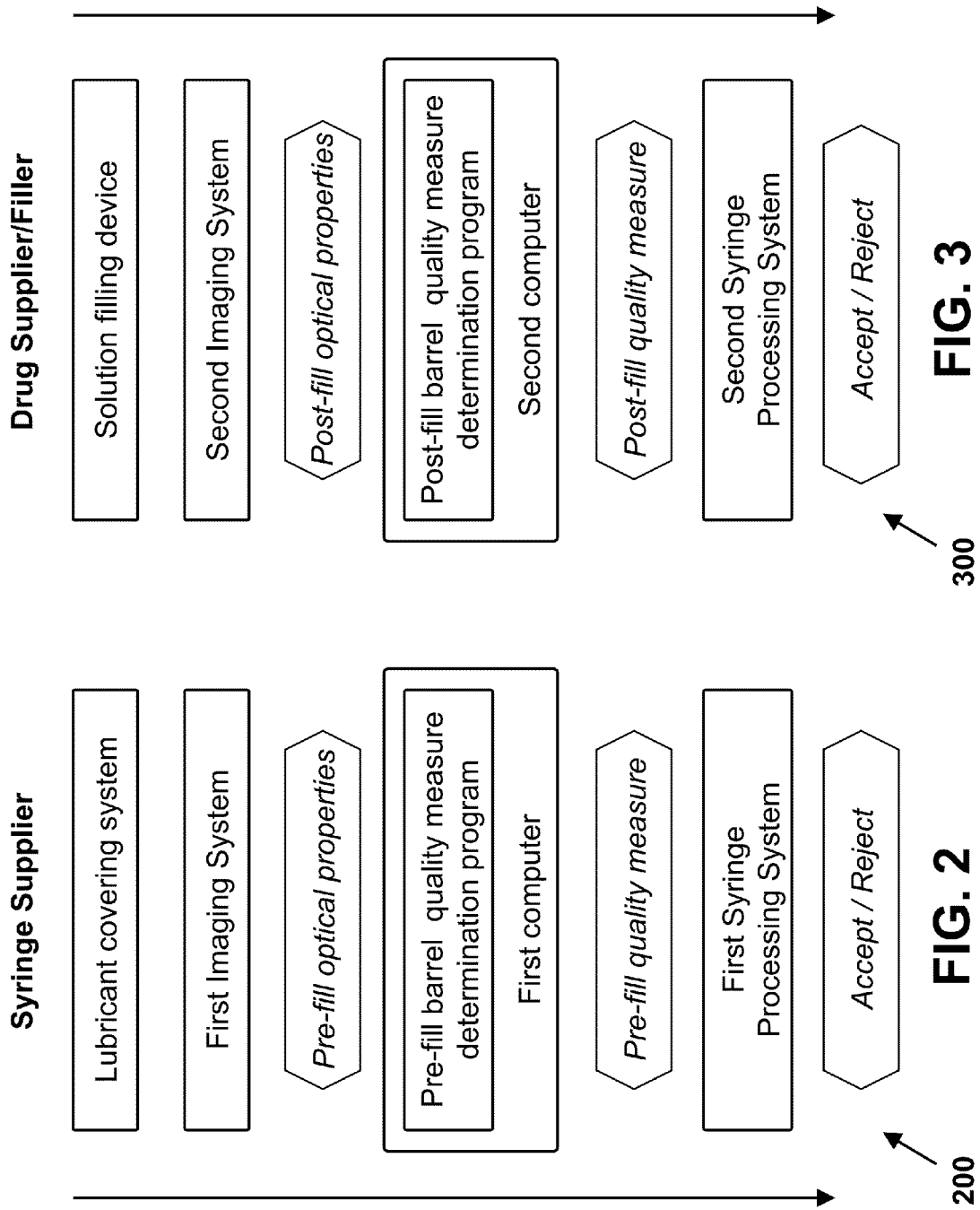
FIG. 2 shows a flow diagram 200 involving the systems/devices involved in pre-fill barrel lubricant coverage testing according to an exemplary embodiment of the invention. The arrow indicates direction of the flow diagram.
FIG. 3 shows a flow diagram 300 involving the systems/devices involved in post-fill barrel lubricant coverage testing according to an exemplary embodiment of the invention. The arrow indicates direction of the flow diagram.
Figure 4:
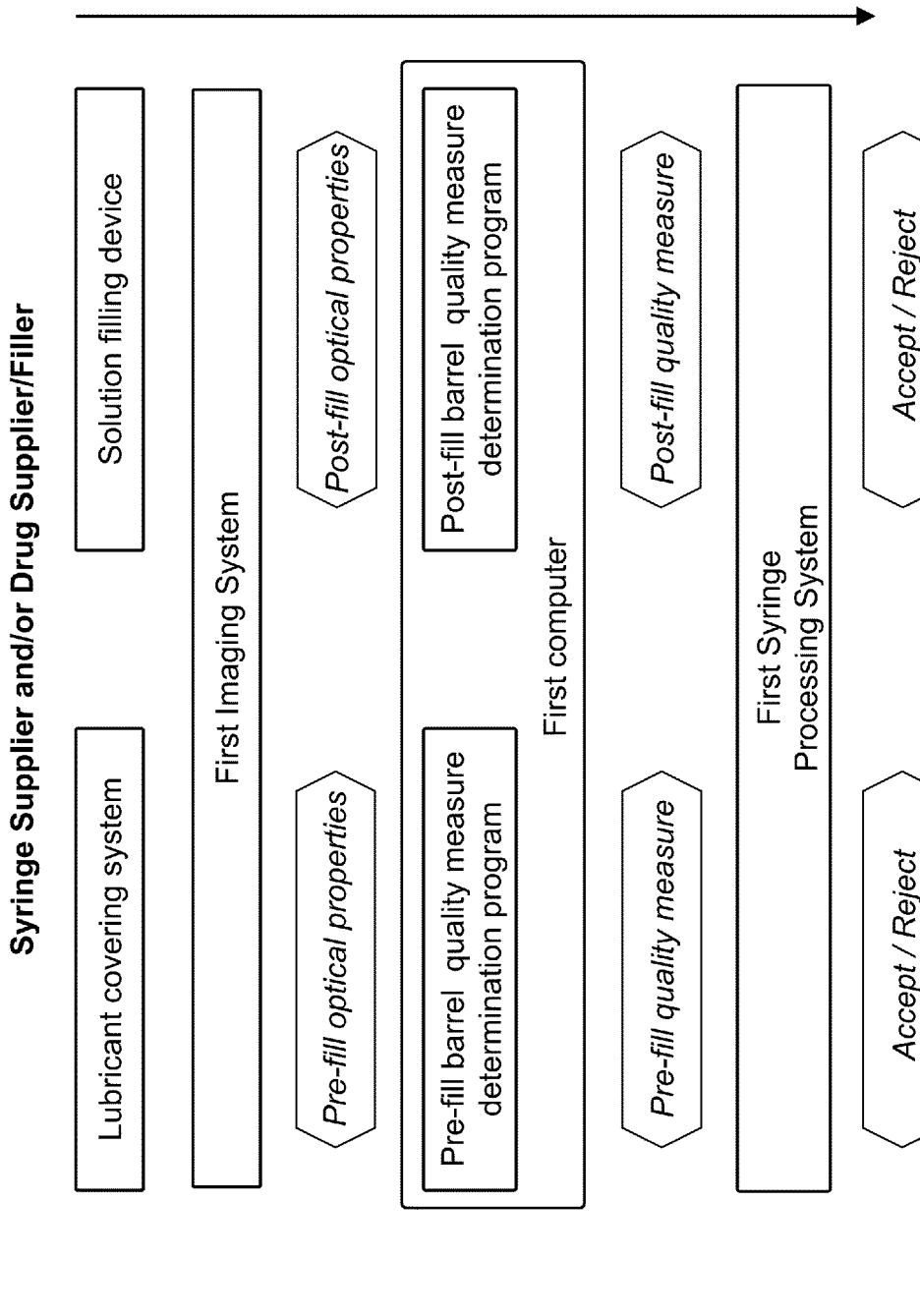
FIG. 4 shows a flow diagram 400 involving the systems/devices involved in pre-fill and post-fill barrel lubricant coverage testing according to an exemplary embodiment of the invention. The arrow indicates direction of the flow diagram.
Figure 5:
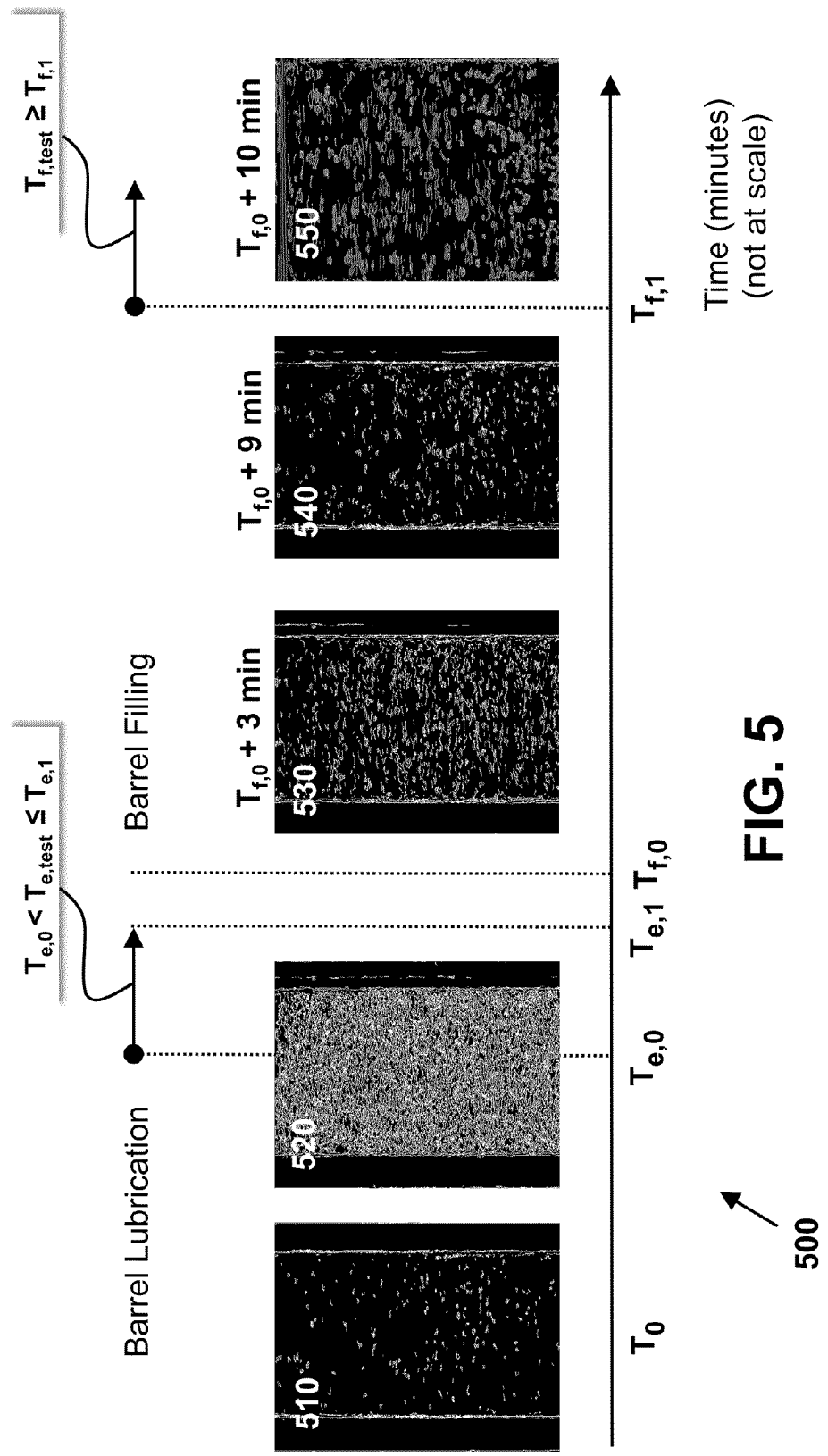
FIG. 5 shows a timeline 500 of images for a plastic syringe barrel obtained by the imaging systems at different time steps of the pre-fill and post-fill barrel lubricant coverage testing process according to an exemplary embodiment of the invention.
Figure 6:
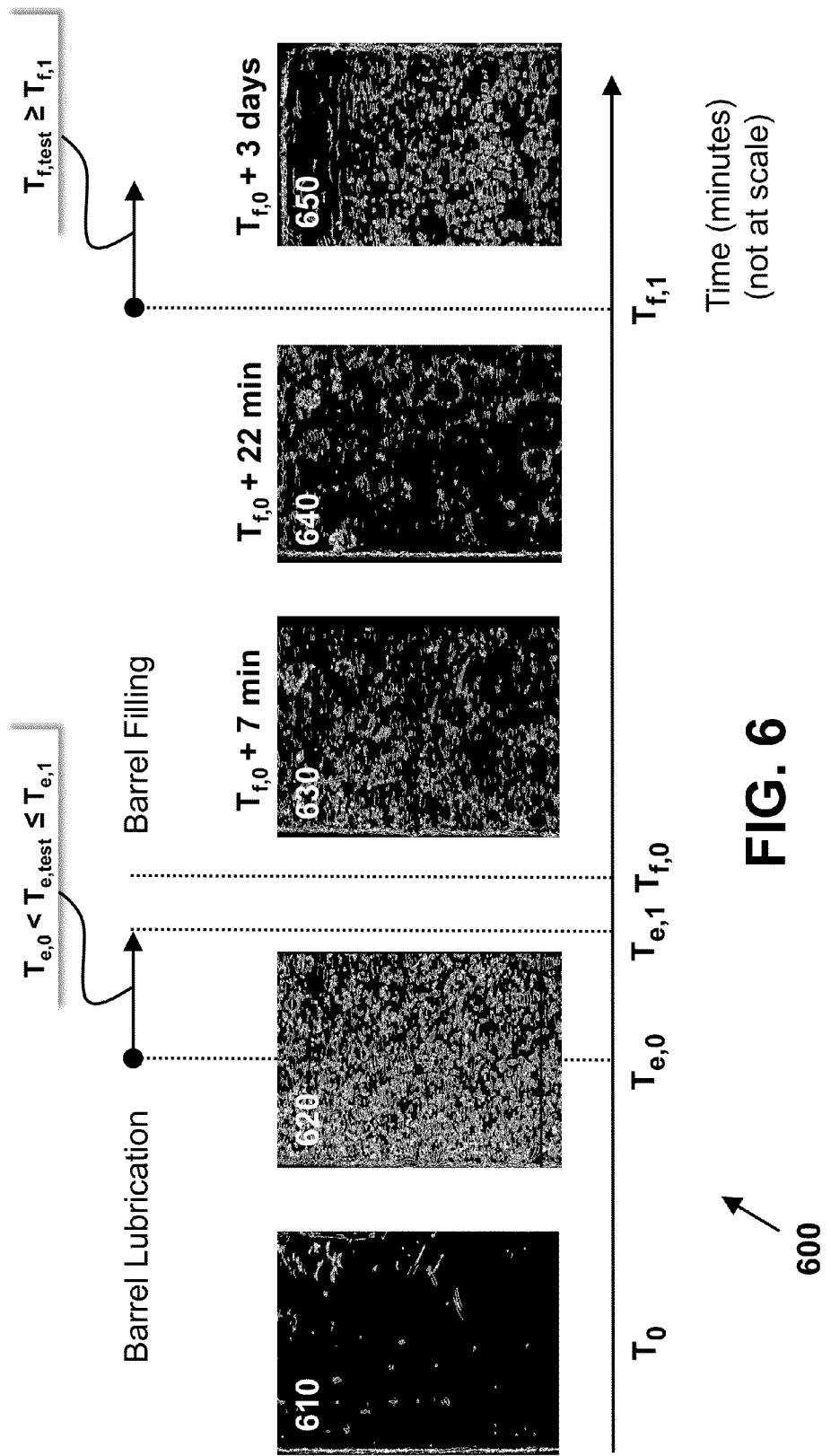
FIG. 6 shows a timeline 600 of images for a glass syringe barrel obtained by the imaging systems at different time steps of the pre-fill and post-fill barrel lubricant coverage testing process according to an exemplary embodiment of the invention.

Upon the manufacturing of a syringe barrel, a lubricant is applied ($T_{e,0}$) to the inner surface of the barrel using a lubricant covering system (FIGS. 1-6). An imaging system is then used immediately after the barrel lubrication to obtain one or more pre-fill optical properties, i.e., prior to the filling of the barrel with an aqueous-based solution. As mentioned infra, the timing of testing ($T_{e,test}$) for adequate coverage is not intuitive and needs to occur on or before $T_{e,1}$ (FIGS. 1, 5-6).

When the barrel is sprayed with oil, the oil arrives on the inside barrel surface as droplets. The droplets are visible because of refractive index changes caused by the presence of droplets. The droplets merge into a uniform oil layer with time and the uniform oil layer does not show any detectable features related to the oil lubrication. Only the defects in the barrel are visible when the oil layer is uniform. A comparison of images 530/540 or 630/640 (image after $T_{e,test}$) with respectively images 510 or 610 (empty pre-lubricated barrel) in respectively FIG. 5 or FIG. 6 illustrates these effects and stresses the importance as it becomes clear that delayed testing beyond $T_{e,test}$ will result in incorrectly concluding that the barrel has no or insufficient oil coverage where in fact it was adequately covered as evidenced by images 520 or 620 in respectively FIG. 5 or FIG. 6. A barrel without performing a timely $T_{e,test}$ could have been rejected or another application of a lubricant could have been applied resulting in too much lubricant coverage as discussed infra.

In general, the time $T_{e,test}$ is defined as $$T_{e,0} < T_{e,test} \leq T_{e,1},$$

where $T_{e,0}$ is the time of applying the lubricant, where $$T_{e,1} = 0.05\eta$$

defined in minutes, and where $\eta$ is a viscosity of the applied lubricant defined in cSt. The pre-fill optical properties are, for example, optical changes related to the applied lubricant, changes in refractive index, or optical features of the lubricant.

The optimum time for inspection of empty (pre-fill) yet lubricated barrels depends on the viscosity of the lubricant. According to the formula the optimum time for inspection of an empty barrel for a lubricant with a viscosity of 20 cSt is less than 1 minute and for a lubricant with a viscosity of 1000 cSt is less than 50 minutes.

A pre-fill quality measure (e.g., average number of features detected per $cm^2$, see also infra) is determined for the lubricant-covered barrel using one or more of the pre-fill optical properties as input to a computer-implemented pre-fill barrel quality measure determination program executed on a computer. A syringe processing system to reject or accept the lubricant-covered barrel based on a predetermined pre-fill quality threshold uses the pre-fill quality measure as input.

Barrel Filling

Upon barrel lubrication, the barrel is filled ($T_{f,0}$) with an aqueous-based solution (e.g., a drug solubilized in water) using a solution filling device (FIGS. 1-6). An imaging system is then used after the barrel filling to obtain one or more post-fill optical properties, i.e., post to the filling of the barrel with an aqueous-based solution. As mentioned infra the timing of testing ($T_{f,test}$) for adequate coverage is not intuitive and needs to occur on or after $T_{f,1}$ (FIGS. 1, 5-6). In other words, in contrast to the pre-fill testing, the post-fill test is not immediately after the barrel filling, but significantly delayed.

In the post-fill testing case the uniform layer of oil starts to bead up over time because oil and water are immiscible. When the beads start to form the image becomes visible because of the changes in the optical features (e.g., refractive index) (550 or 650 in respectively FIG. 5 or FIG. 6). It is noted that this post-fill evaluation process is the reverse of the physical/chemical process (beads to uniform oil layer) described infra for the pre-fill evaluation process of empty barrels with oil. In other words, the post-fill test has to be done on or after a certain amount of time ($T_{f,test}$) to see the beads of oil at the inner surface of the barrel. A post-fill barrel without performing the test on or after $T_{f,test}$ could have been rejected or another application of a lubricant could have been applied resulting in too much lubricant coverage as discussed infra.

For the case of the filled glass barrel with 1000 cSt viscosity oil, inspecting the barrel for the presence of oil in a shorter time than 3 days would lead to the conclusion that there is no oil in the barrel because the oil droplets would not yet have formed and the image would show little to no detectable features.

In general, the time $T_{f,test}$ is defined as $$T_{f,test} \geq T_{f,1},$$

where $$T_{f,1} = 8.8 \exp(0.0063\eta)$$

defined in minutes and defined from $T_{f,0}$, where $\eta$ is the viscosity of the applied lubricant and defined in cSt, and where $T_{f,0}$ is the time of the filling the aqueous-based solution. The post-fill optical properties are, for example optical changes related to the applied lubricant, changes in refractive index or optical features of the lubricant.

A post-fill quality measure (e.g., average number of features detected per $cm^2$, see also infra) is determined for the lubricant-covered barrel using one or more of the post-fill optical properties as input to a computer-implemented post-fill barrel quality measure determination program executed on a computer. A syringe processing system to reject or accept the filled lubricant-covered barrel based on a predetermined post-fill quality threshold uses the post-fill quality measure as input.

Implementations

FIG. 2 shows an example where the pre-fill testing is performed at the syringe supplier company using its own lubricant filling system, imaging system, computer, and syringe processing system respectively referred to as first. FIG. 3 shows an example where the post-fill testing is performed at the syringe filling or drug supplier company using its own solution filling device, imaging system, computer, and syringe processing system respectively referred to as second. FIG. 4 shows an example where the pre-fill and post-fill testing are performed at the same company or facility using a its own lubricant covering system, solution filling device, imaging system, a computer, and a syringe processing system respectively and where applicable referred to as first. A person skilled in the art would appreciate that different scenarios and combination of devices/systems can be used to fulfill the testing requirements of this invention.

Exemplary Results

FIG. 5 shows a timeline 500 of images for a plastic syringe barrel (West Pharma 1 mL Long Syringe, 51.6×8.15 mm) obtained by the imaging systems at different time steps of the pre-fill and post-fill barrel lubricant coverage testing process according to an exemplary embodiment of the invention. Image 510 is of an empty/pre-fill syringe barrel at time $T_0$, image 520 is of a pre-fill barrel containing lubricant on the interior surface of the barrel immediately after spraying with oil at time $T_{e,0}$, image 530 is of a post-fill barrel containing lubricant on the interior surface of the barrel 3 minutes after filling ($T_{f,0}$) with an aqueous-based solution at time $T_{f,0}+3$ minutes, image 540 is of a post-fill barrel containing lubricant on the interior surface of the barrel 9 minutes after filling ($T_{f,0}$) with an aqueous-based solution at time $T_{f,0}+9$ minutes, and image 550 is of a post-fill barrel containing lubricant on the interior surface of the barrel 10 minutes after filling ($T_{f,0}$) with an aqueous-based solution at time $T_{f,0}+10$ minutes.

FIG. 6 shows a timeline 600 of images for a glass syringe barrel (Schott glass, 2.25 mL, 54.4×10.85 mm) obtained by the imaging systems at different time steps of the pre-fill and post-fill barrel lubricant coverage testing process according to an exemplary embodiment of the invention. Image 610 is of an empty/pre-fill syringe barrel at time $T_0$, image 620 is of a pre-fill barrel containing lubricant on the interior surface of the barrel immediately after spraying with oil at time $T_{e,0}$, image 630 is of a post-fill barrel containing lubricant on the interior surface of the barrel 7 minutes after filling ($T_{f,0}$) with an aqueous-based solution at time $T_{f,0}+7$ minutes, image 640 is of a post-fill barrel containing lubricant on the interior surface of the barrel 22 minutes after filling ($T_{f,0}$) with an aqueous-based solution at time $T_{f,0}+22$ minutes, and image 650 is of a post-fill barrel containing lubricant on the interior surface of the barrel 3 days after filling ($T_{f,0}$) with an aqueous-based solution at time $T_{f,0}+3$ days.

Figure 7:
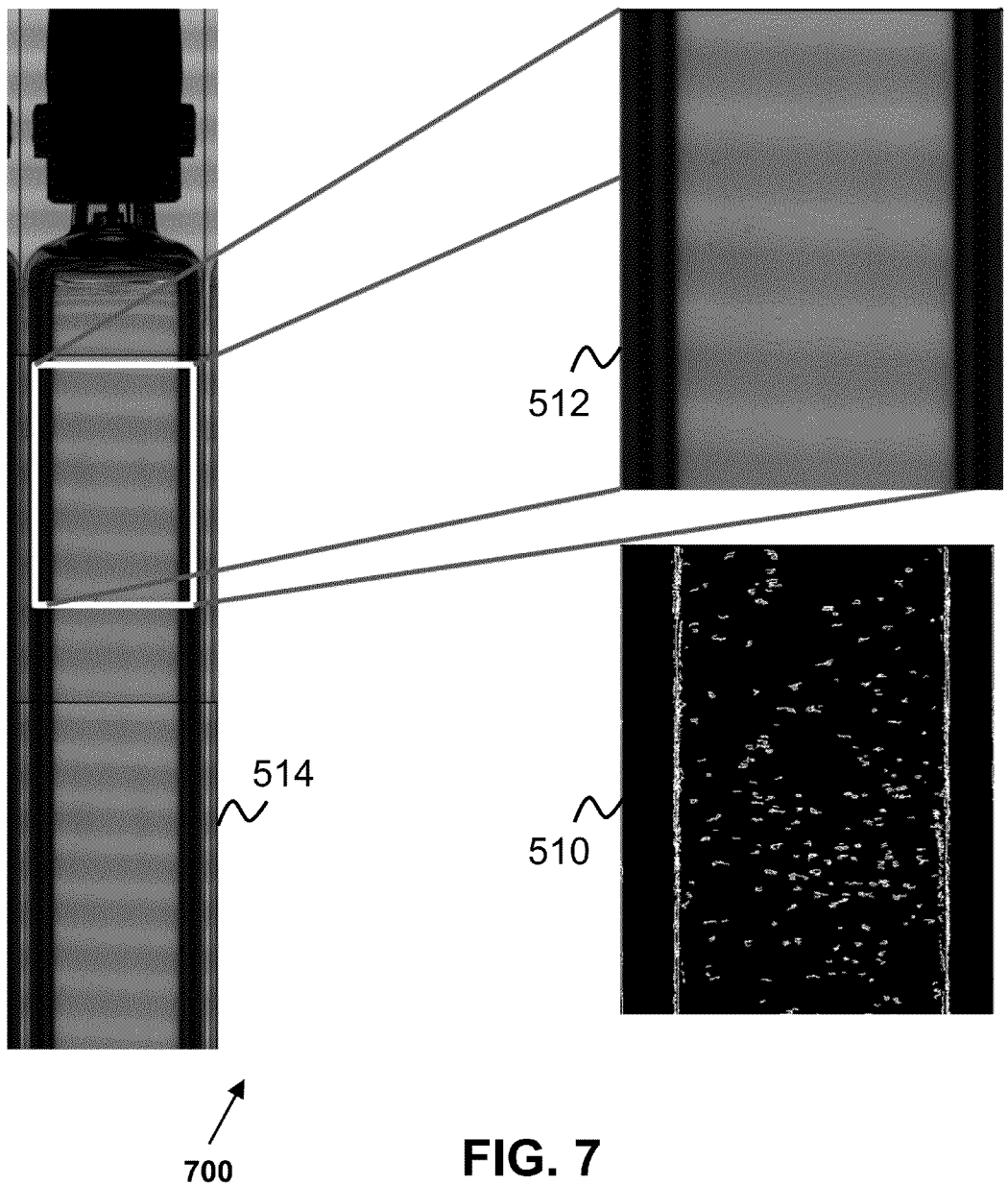
FIG. 7 shows according to an exemplary embodiment of the invention images 700 of an empty/pre-fill plastic syringe barrel (without lubricant).

FIG. 7 shows according to an exemplary embodiment of the invention images 700 of an empty/pre-fill plastic syringe barrel at time $T_{e,0}$ (without lubricant). Image 510 is a computer-processed version of 512, which itself is an enlarged version of image 514 obtained from the syringe barrel. The images are homogeneous with alternating dark and light regions caused by the presence of the mask, which is a 10 cm by 10 cm by 1 cm aluminum block with 1 mm straight grooves cut through the aluminum. An edge detection algorithm, the process applied to image 510, shows a small number of plastic molding defects in the empty barrel, which cause changes in the refractive index.

Figure 8:
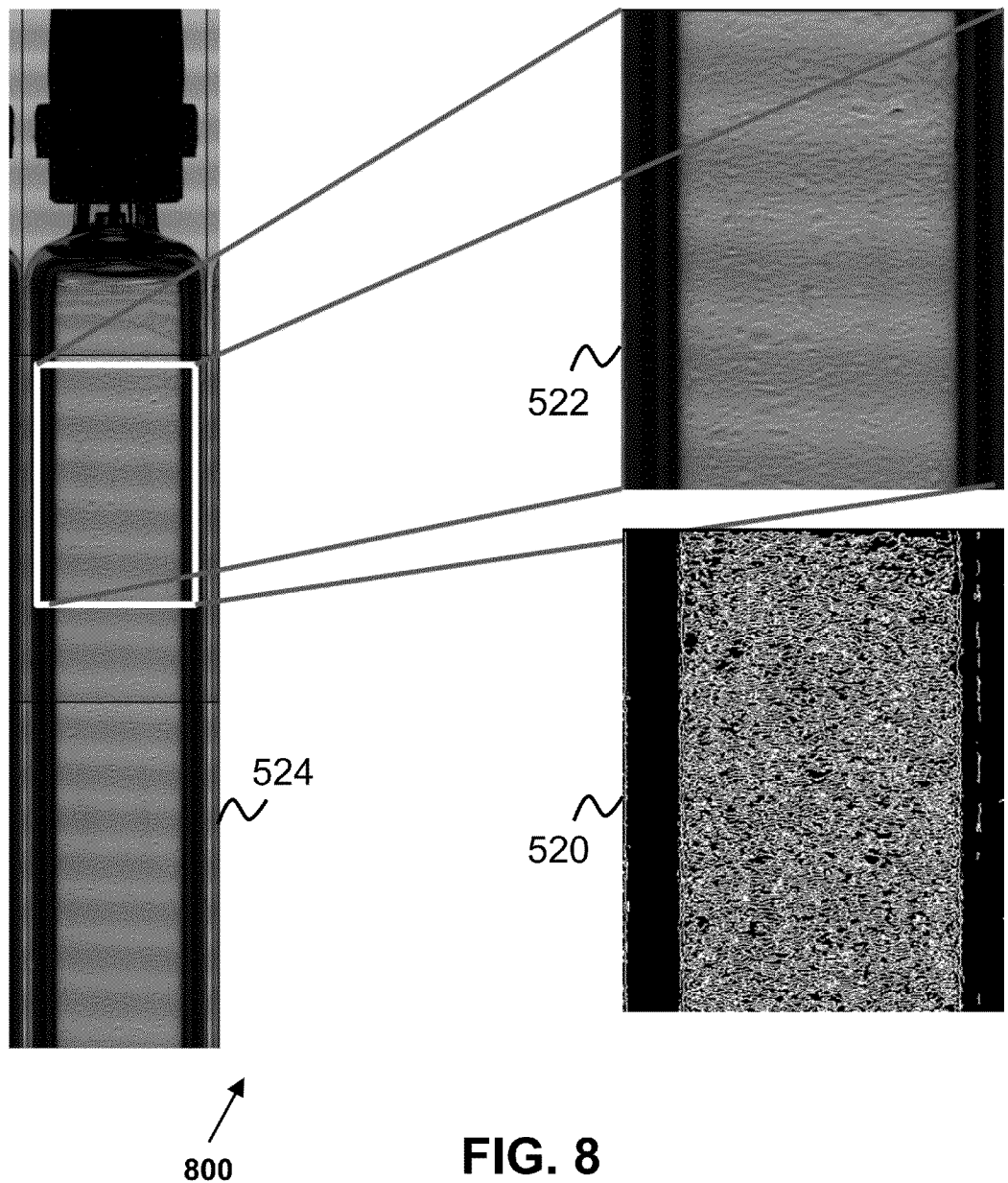
FIG. 8 shows according to an exemplary embodiment of the invention images 800 of a pre-fill plastic barrel containing lubricant on the interior surface of the barrel immediately after spraying with oil.

FIG. 8 shows according to an exemplary embodiment of the invention images 800 of a pre-fill plastic barrel containing lubricant on the interior surface of the barrel immediately after spraying with oil at time $T_{e,0}$. Image 520 is a computer-processed version of 522, which itself is an enlarged version of image 524 obtained from the syringe barrel. 20 cSt viscosity oil was used for lubrication. The images obtained immediately after spraying with oil, indicate a distribution of oil droplets in the empty barrel. The edges of individual oil droplets are determined using an edge detection algorithm, as shown in image 520.

Figure 9:
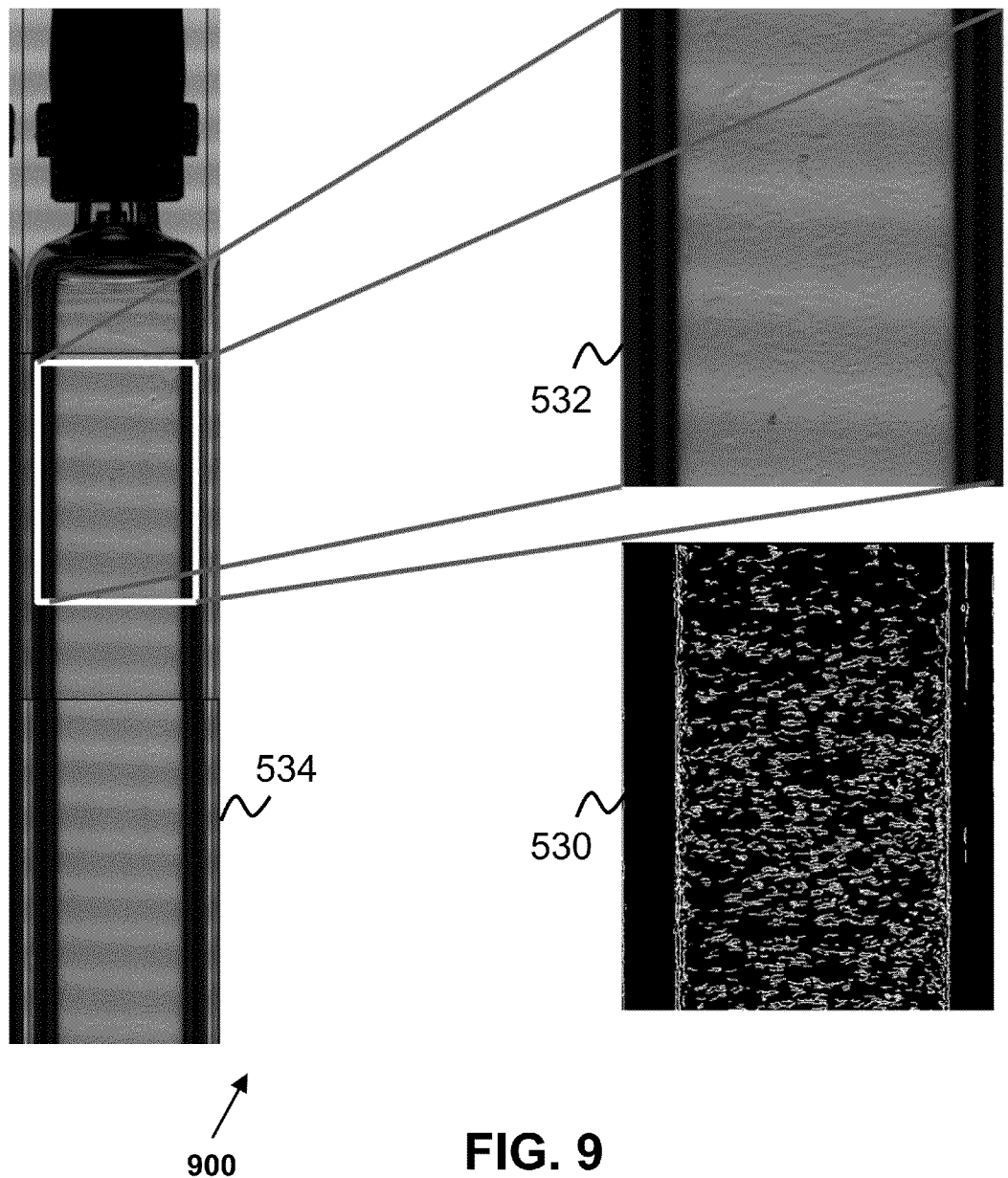
FIG. 9 shows according to an exemplary embodiment of the invention images 900 of a post-fill barrel containing lubricant on the interior surface of the barrel 3 minutes after filling with an aqueous-based solution.

FIG. 9 shows according to an exemplary embodiment of the invention images 900 of a post-fill barrel containing lubricant on the interior surface of the barrel 3 minutes after filling ($T_{f,0}$) with an aqueous-based solution at time $T_{f,0}+3$ minutes. Image 530 is a computer-processed version of 532, which itself is an enlarged version of image 534 obtained from the syringe barrel. 20 cSt viscosity oil was used for lubrication.

Figure 10:
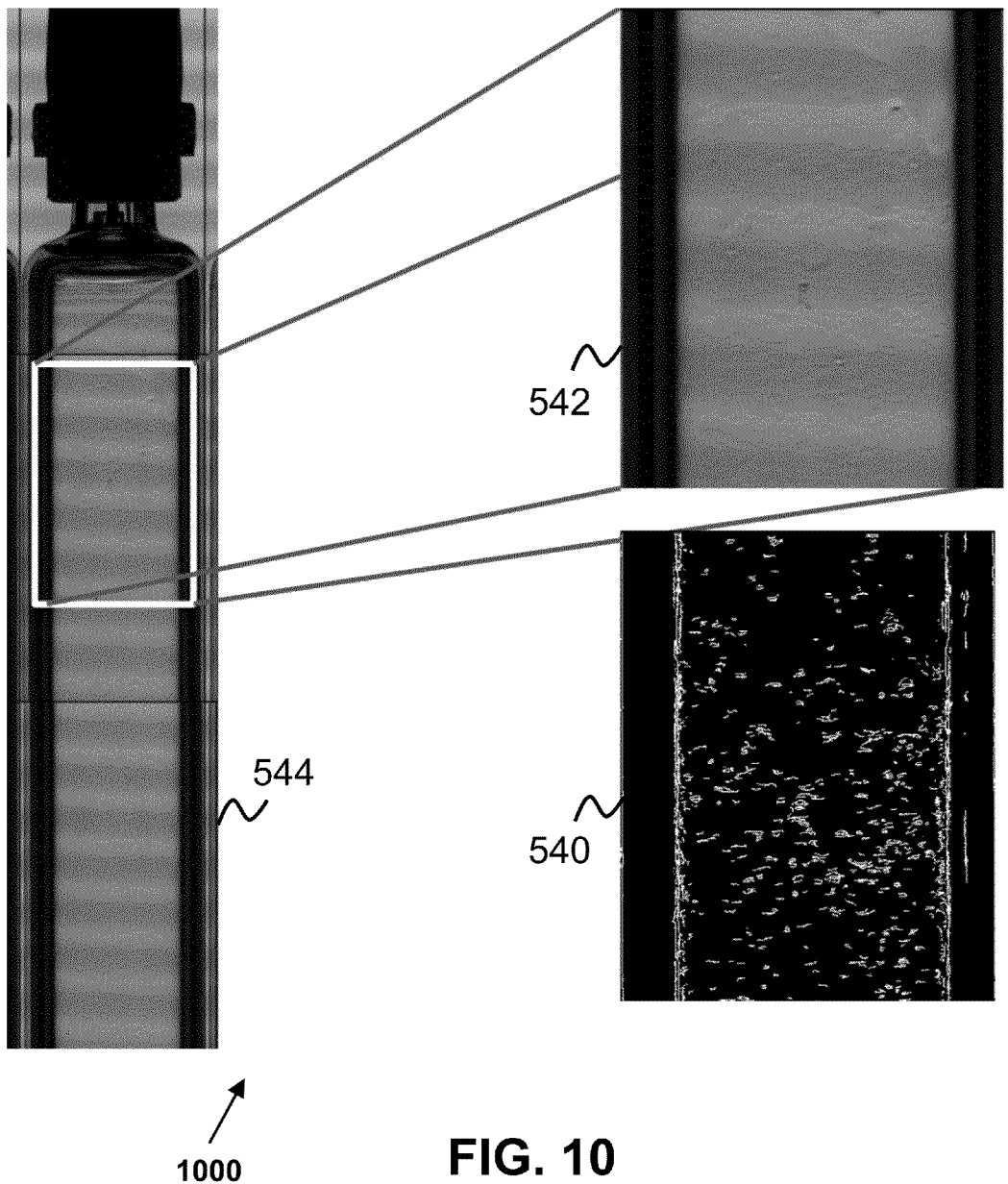
FIG. 10 shows according to an exemplary embodiment of the invention images 1000 of a post-fill barrel containing lubricant on the interior surface of the barrel 9 minutes after filling with an aqueous-based solution.

FIG. 10 shows according to an exemplary embodiment of the invention images 1000 of a post-fill barrel containing lubricant on the interior surface of the barrel 9 minutes after filling ($T_{f,0}$) with an aqueous-based solution at time $T_{f,0}+9$ minutes. Image 540 is a computer-processed version of 542, which itself is an enlarged version of image 544 obtained from the syringe barrel. 20 cSt viscosity oil was used for lubrication.

The images of the empty plastic barrel after respectively 3 minutes and 9 minutes (FIGS. 9-10) show that droplet coalescence has already taken place and there is less evidence of individual droplets. In these regions it is not clear whether there is lubricant present since the coalesced droplets have a uniform refractive index and the image becomes similar to FIG. 7 for the empty plastic barrel.

Figure 11:
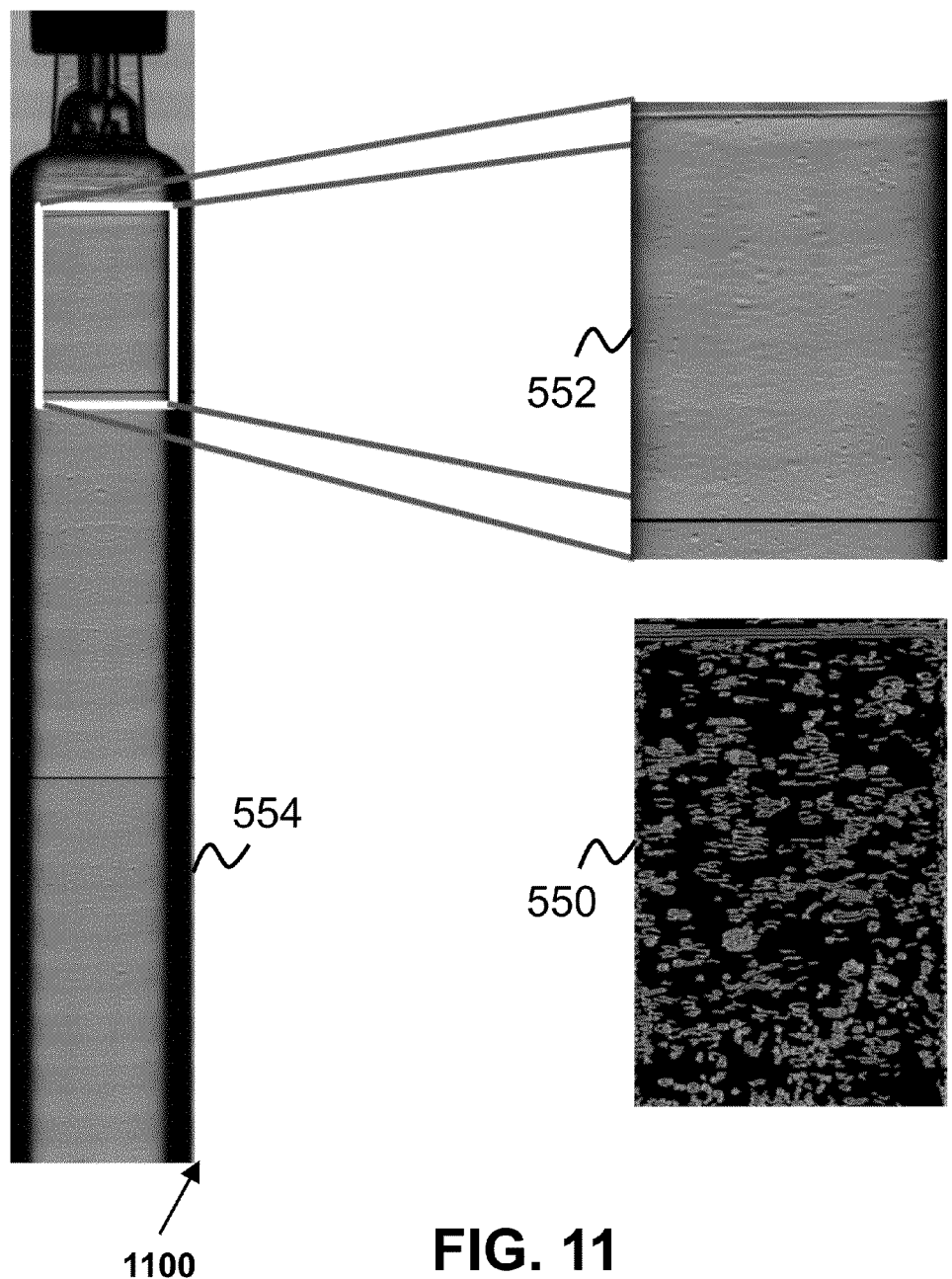
FIG. 11 shows according to an exemplary embodiment of the invention images 1100 of a post-fill barrel containing lubricant on the interior surface of the barrel 10 minutes after filling with an aqueous-based solution.

FIG. 11 shows according to an exemplary embodiment of the invention images 1100 of a post-fill barrel containing lubricant on the interior surface of the barrel 10 minutes after filling ($T_{f,0}$) with an aqueous-based solution at time $T_{f,0}+10$ minutes. Image 550 is a computer-processed version of 552, which itself is an enlarged version of image 554 obtained from the syringe barrel. 20 cSt viscosity oil was used for lubrication. An aqueous solution was used for filling. The images show oil beading into droplets after 10 minutes because water and oil are immiscible, verifying the presence of oil in the plastic barrel.

Figure 12:
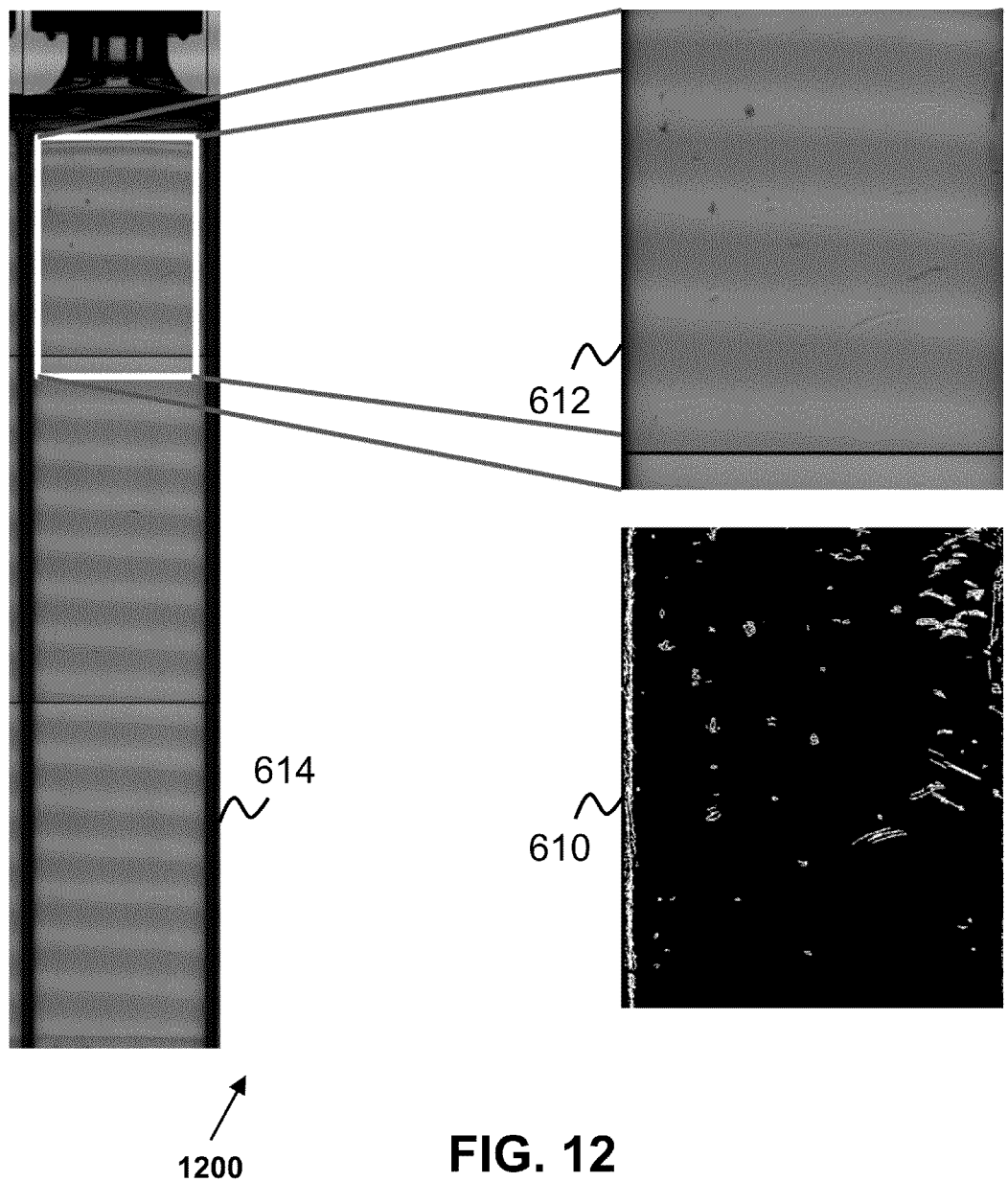
FIG. 12 shows according to an exemplary embodiment of the invention images 1200 of an empty/pre-fill glass syringe barrel (without lubricant).

FIG. 12 shows according to an exemplary embodiment of the invention images 1200 of an empty/pre-fill glass syringe barrel at time $T_{e,0}$ (without lubricant). Image 610 is a computer-processed version of 612, which itself is an enlarged version of image 614 obtained from the syringe barrel. An edge detection algorithm, the process applied on image 610, shows the presence of defects in the glass as well as external impurities attached to the inside or outside glass wall.

Figure 13:
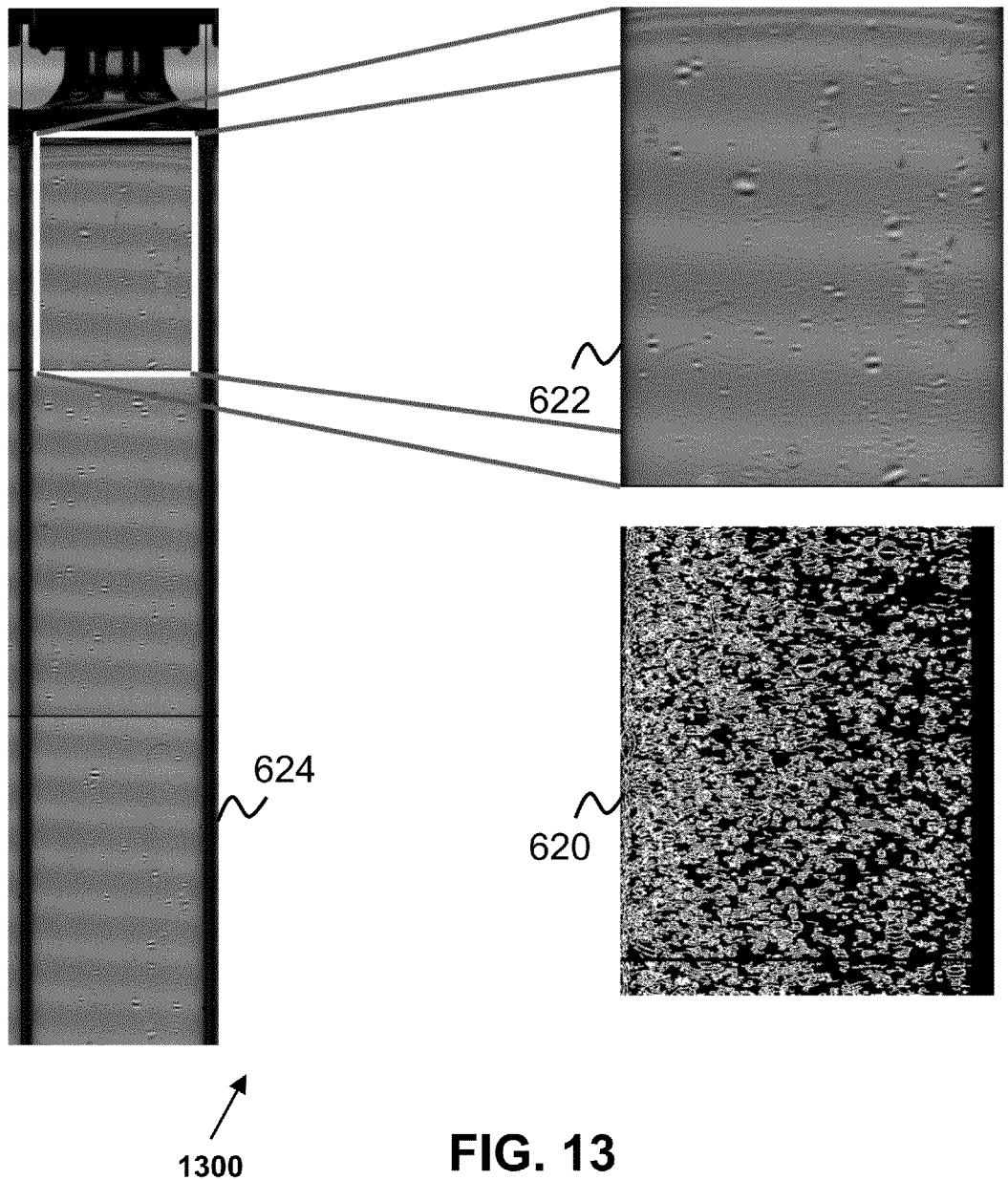
FIG. 13 shows according to an exemplary embodiment of the invention images 1300 of a pre-fill glass barrel containing lubricant on the interior surface of the barrel immediately after spraying with oil.

FIG. 13 shows according to an exemplary embodiment of the invention images 1300 of a pre-fill glass barrel containing lubricant on the interior surface of the barrel immediately after spraying with oil at time $T_{e,0}$. Image 620 is a computer-processed version of 622, which itself is an enlarged version of image 624 obtained from the syringe barrel. 1000 cSt viscosity oil was used for lubrication. The images obtained immediately after spraying with oil, indicate a distribution of oil droplets in the empty barrel. The edges of individual oil droplets are determined using an edge detection algorithm, as shown in image 620.

Figure 14:
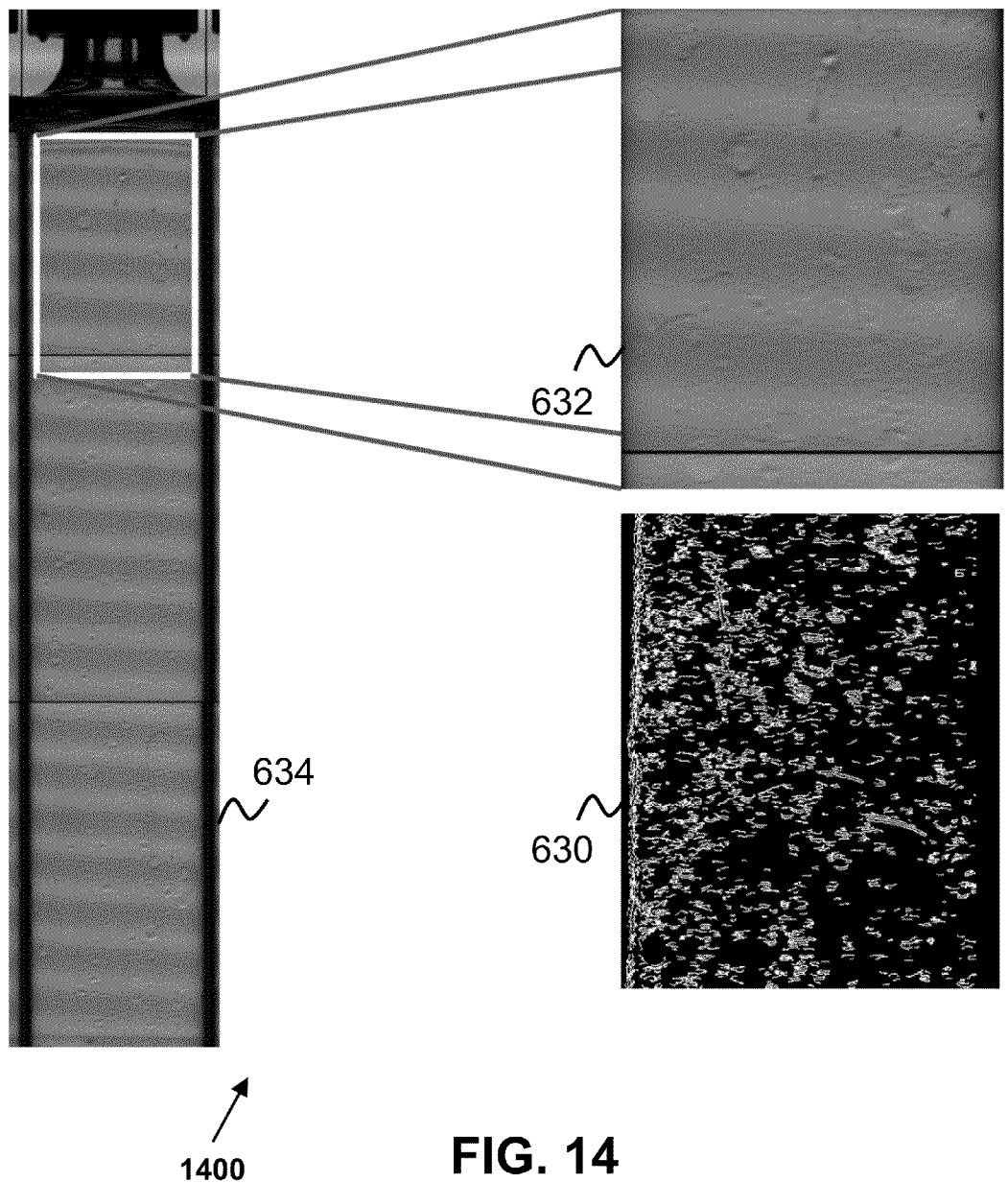
FIG. 14 shows according to an exemplary embodiment of the invention images 1400 of a post-fill barrel containing lubricant on the interior surface of the barrel 7 minutes after filling with an aqueous-based solution.

FIG. 14 shows according to an exemplary embodiment of the invention images 1400 of a post-fill barrel containing lubricant on the interior surface of the barrel 7 minutes after filling ($T_{f,0}$) with an aqueous-based solution at time $T_{f,0}+7$ minutes. Image 630 is a computer-processed version of 632, which itself is an enlarged version of image 634 obtained from the syringe barrel. 1000 cSt viscosity oil was used for lubrication.

Figure 15:
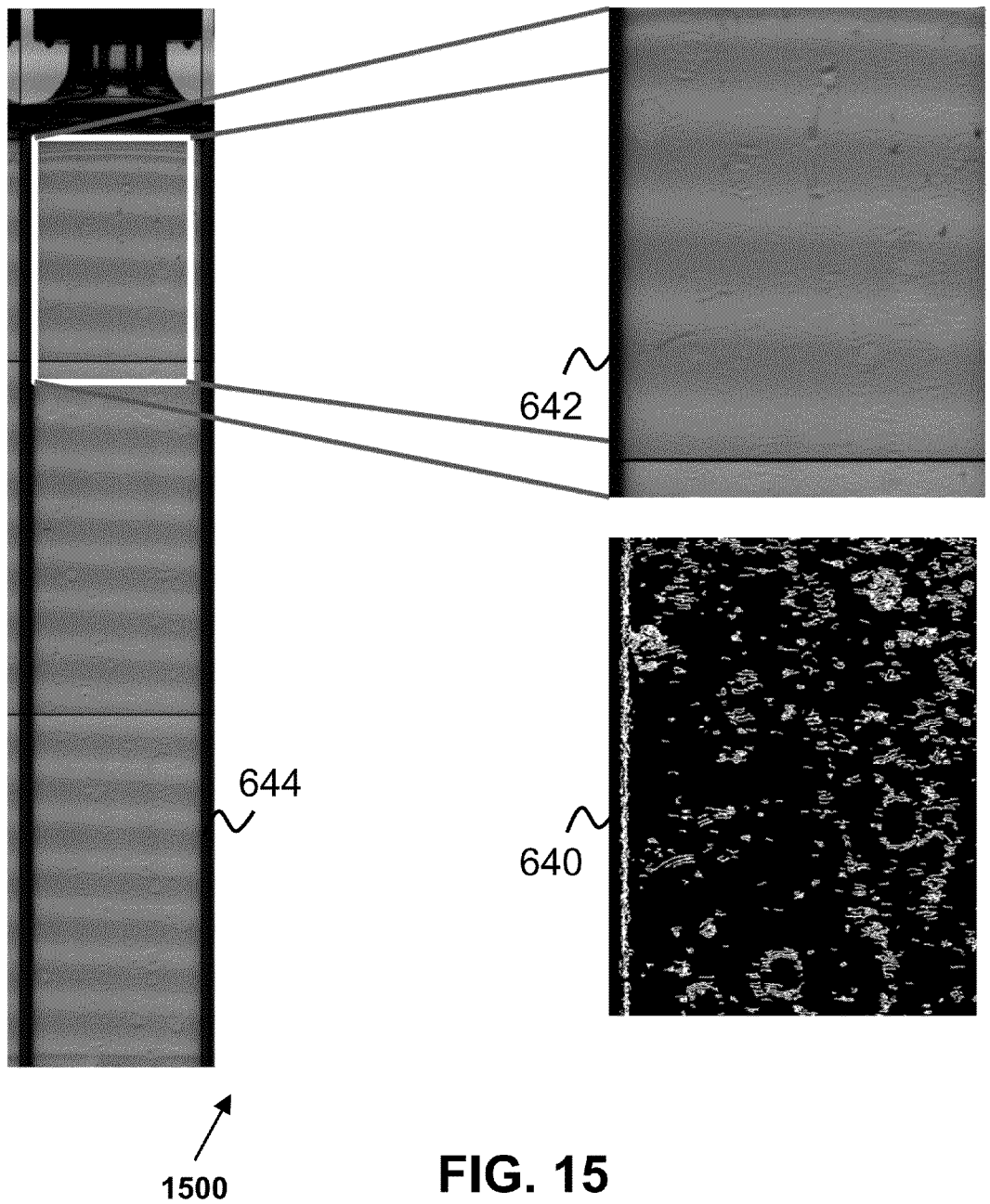
FIG. 15 shows according to an exemplary embodiment of the invention images 1500 of a post-fill barrel containing lubricant on the interior surface of the barrel 22 minutes after filling with an aqueous-based solution.

FIG. 15 shows according to an exemplary embodiment of the invention images 1500 of a post-fill barrel containing lubricant on the interior surface of the barrel 22 minutes after filling ($T_{f,0}$) with an aqueous-based solution at time $T_{f,0}+22$ minutes. Image 640 is a computer-processed version of 642, which itself is an enlarged version of image 644 obtained from the syringe barrel. 1000 cSt viscosity oil was used for lubrication.

The images of the empty glass barrel after respectively 7 minutes and 22 minutes (FIGS. 14 and 15) show that droplet coalescence has already taken place and there is less evidence of individual droplets. In these regions it is not clear whether there is lubricant present since the coalesced droplets have a uniform refractive index and the image becomes similar to FIG. 12 for the empty glass barrel.

Figure 16:
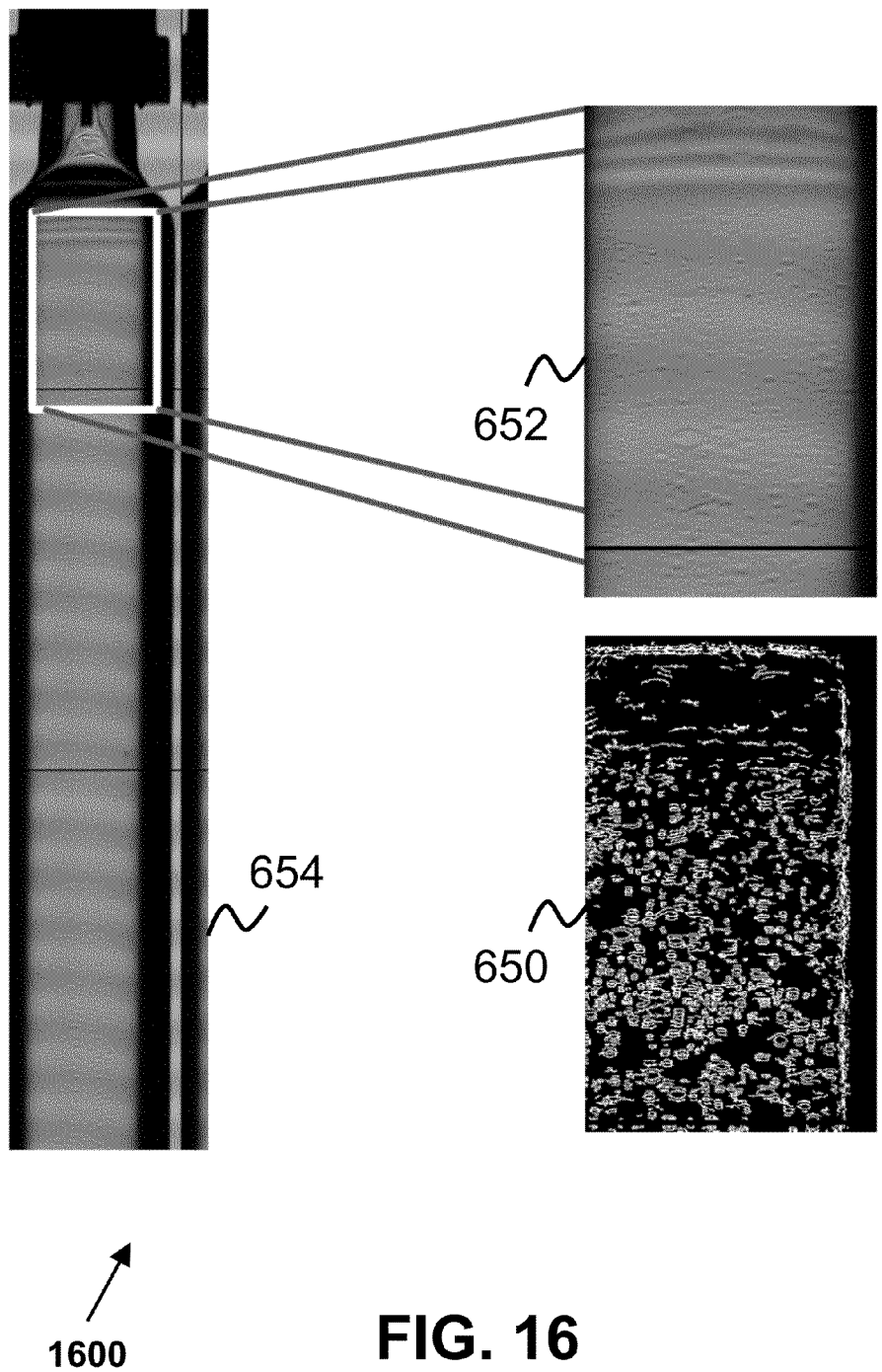
FIG. 16 shows according to an exemplary embodiment of the invention images 1600 of a post-fill barrel containing lubricant on the interior surface of the barrel 3 days after filling with an aqueous-based solution.
Figure 17:
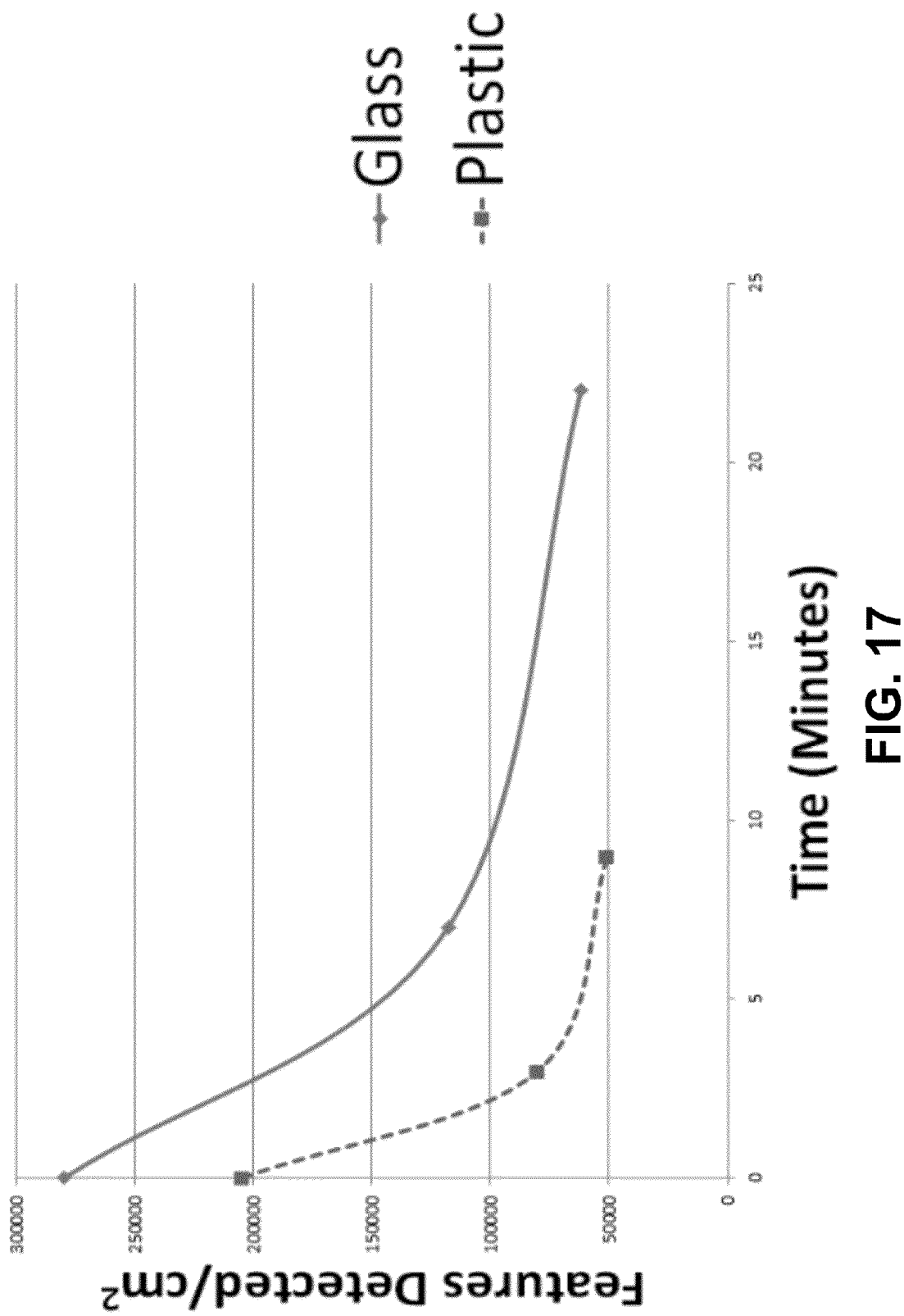
FIG. 17 shows according to an exemplary embodiment according to the invention the time decay of detected optical features in an empty (pre-fill) plastic and glass syringe barrel after spraying the interior surface of the barrel with oil of viscosity 20 cSt.
Figure 18:
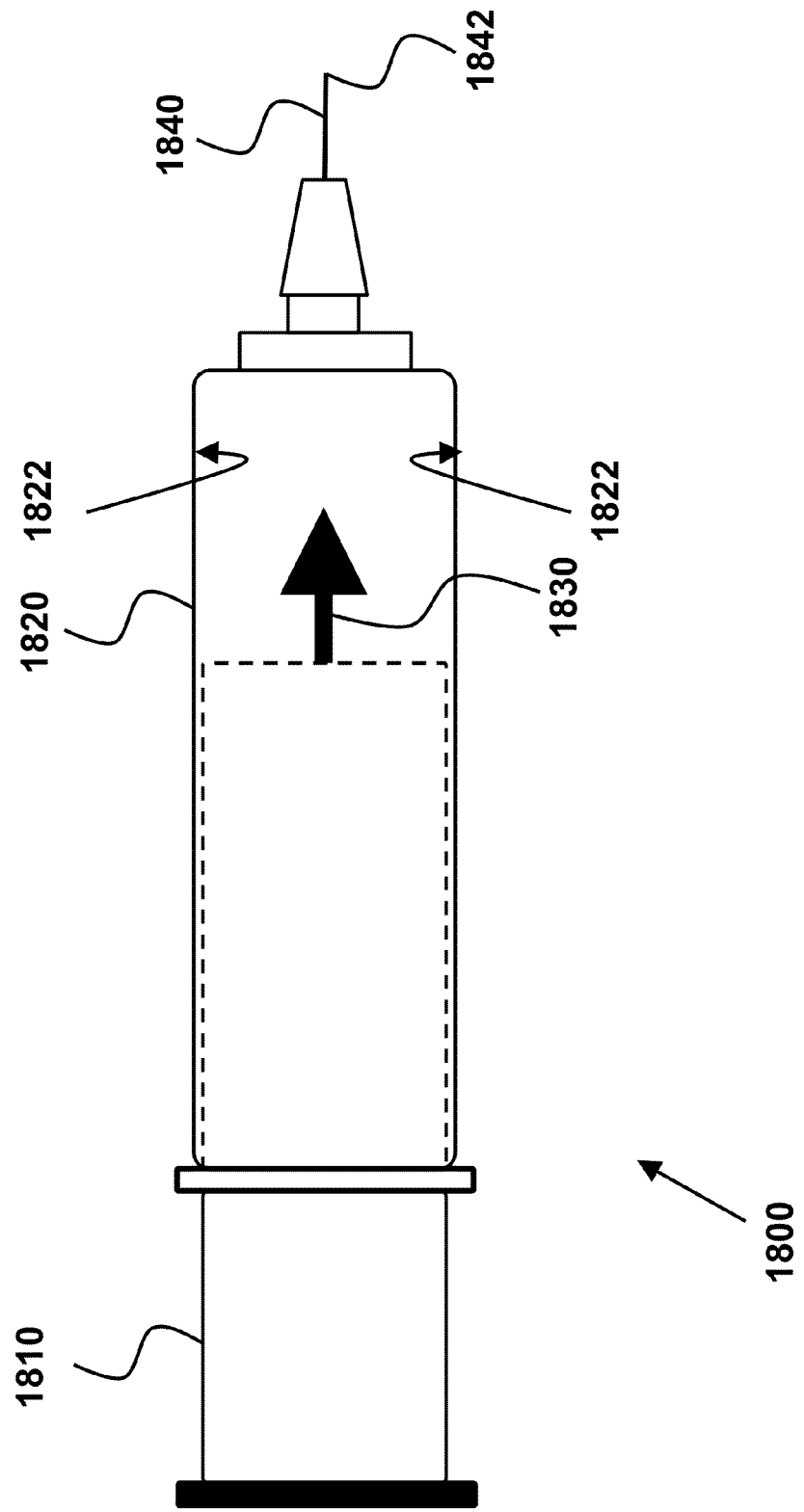
FIG. 18 shows a syringe according to an exemplary embodiment according to the invention.
Figure 19:
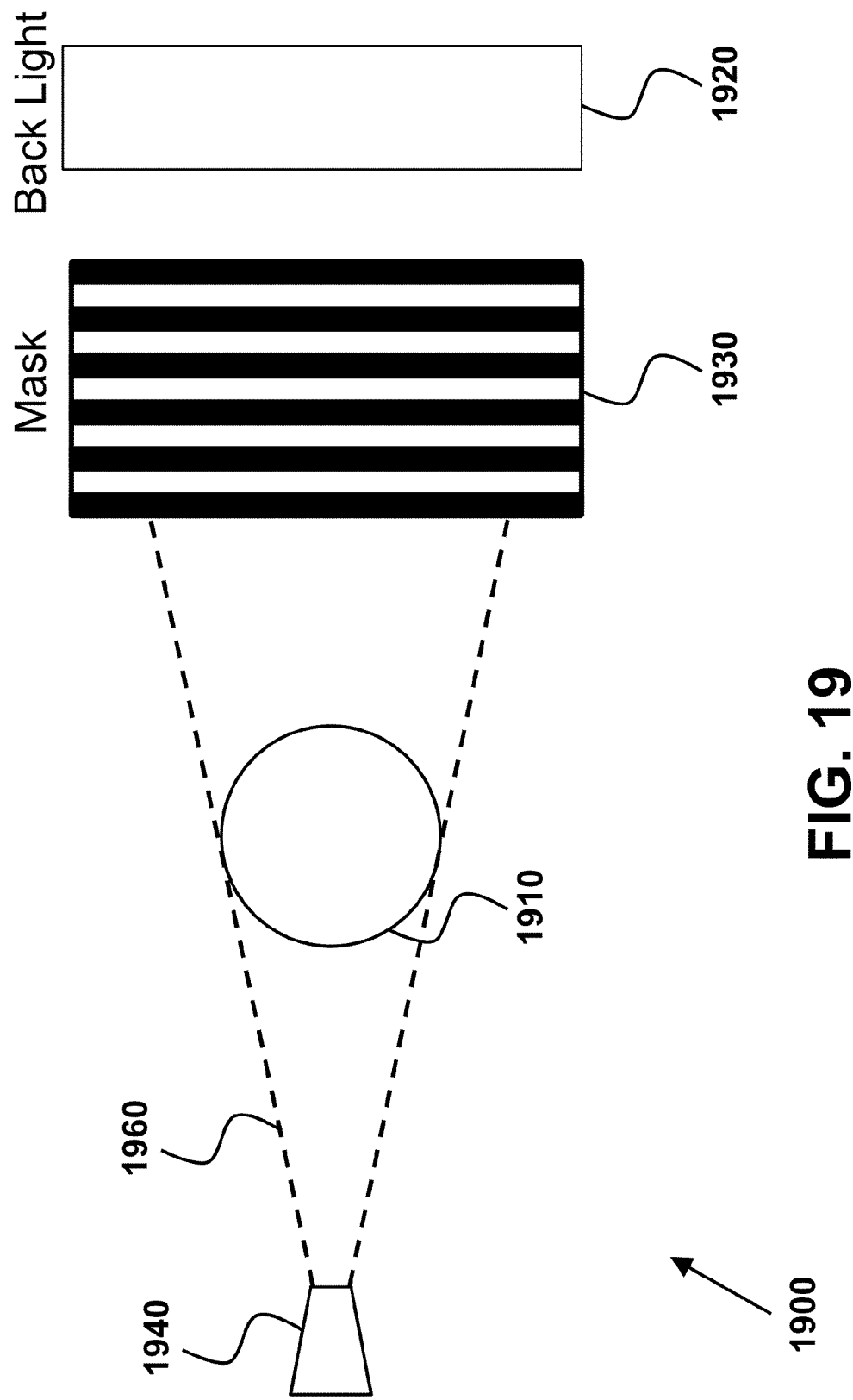
FIG. 19 shows an imaging system setup according to an exemplary embodiment according to the invention.

FIG. 16 shows according to an exemplary embodiment of the invention images 1600 of a post-fill barrel containing lubricant on the interior surface of the barrel 3 days after filling ($T_{f,0}$) with an aqueous-based solution at time $T_{f,0}+3$ days.

Image 650 is an enlarged version of 652, which itself is an enlarged version of image 654 obtained from the syringe barrel. 1000 cSt viscosity oil was used for lubrication. An aqueous solution was used for filling. The images show oil beading into droplets after 3 days because water and oil are immiscible, verifying the presence of oil in the glass barrel.

Algorithms: Detection and Analysis

For detection and analysis of the images various techniques can be used as a person skilled in the art would appreciate. For the embodiments presented herein, a low pass filtering (e.g., Median filter, Gaussian blurring) was applied to the input sensor image to reduce high-frequency noise. This was followed by edge detection (e.g., Canny edge detection) to detect features.

The detected edge features can then be quantified in a number of ways to compute quality measures. In general, the one or more pre-fill optical properties and the one or more post-fill optical properties could be optical changes related to the applied lubricant, changes in refractive index or optical features of the lubricant. Examples of quality measures include, but are not limited to:

Number of features detected per $cm^2$,
Number of features detected per radial slice,
Histogram of detected feature sizes, and/or
Number and sizes of gaps (areas containing fewer than some threshold $Thresh_{gaps}$ of features).

Pre-fill and post-fill quality thresholds can be used to accept or reject respectively the pre-filled lubricant-covered barrel and post-filled lubricant-covered barrel. Examples of such thresholds include, but are not limited to:

Accept barrels with an average density d of at least 100000 features/$cm^2$<d, reject otherwise,
Accept barrels with at least 150000 features/$cm^2$ in the first 40% of the barrel (toward the open end) and at least 100000 features/$cm^2$ in the remaining 60% of the barrel, reject otherwise,
Accept barrels where at least 80% of the features are <30 px (e.g., control on droplet size), reject otherwise, and/or
Accept barrels with no more than 15% of the barrel being occupied by a gap (or area containing fewer than some threshold $T_{gaps}$ of features).

Importance of Quality of Testing

The teachings and examples provided herein stress the importance of quality testing of the lubrication layer at the inside of the barrel in the pre-filled stage as well as in the post-filled stage, and not just one or the other. As discussed elsewhere herein, failure to perform these quality tests at both stages may lead to serious consequences, which could manifest when the syringe is used on patients. Poorly lubricated syringes (e.g., a barrel with very sparse lubrication, or a barrel with 50% of its area covered in gaps), for example, may lead to improper dosing if the injection device stalls in the middle of dosing. Manually pushed devices could also be affected as poor lubrication may require more force to be applied than the physical device can handle, breaking, for instance, the plunger rod.

Improvements

To guarantee or significantly improve high-quality coatings for syringe barrels is through 100%, high-speed inspection of pre-filled and post-filled syringes at the time frames specified in this invention, which is clear from the discussions and teachings herein.

Simply taking the approach of testing at the pre-filled stage and post-filled stages are let's say time t, where t is the same time for both tests would lead to serious problems. For example, for t=30 seconds and η is 20 cSt, the pre-fill test would be timely performed, but the post-fill test would be performed too early, resulting is the wrong conclusion from a quality control standpoint. Similarly, for t=15 minutes and η is 20 cSt, the pre-fill test would be performed too late, and the post-fill test would be timely performed, also resulting is the wrong conclusion from a quality control standpoint.

Furthermore, simply taking one test or the other would fail is many different way as the following problems/scenarios could be identified:

Pre-fill accepted incorrectly, no post-fill test. The first problem could be that the pre-filled lubricated syringe could have been accepted incorrectly, by testing passed the specified time pre-fill quality test window, as in fact it should have been rejected. Then if there is no post-fill quality test, this particular syringe would eventually have been used for a patient, as in fact it should not have been used and been rejected.

Pre-fill accepted correctly, but no post-fill test. The second problem could be that the pre-filled lubricated syringe could have been accepted correctly, and then during the period between lubrication and filling with an aqueous-based solution something could have happened to the lubrication coverage resulting in a coverage below the quality threshold, but then if there is no post-fill quality test this particular syringe would have passed on to the patient, incorrectly (defined as when there would have been a post-filled quality test, as embodied in this invention).

Pre-fill rejected incorrectly. The third problem could be that the pre-filled lubricated syringe could have been rejected incorrectly, by testing passed the specified pre-fill quality test window, as in fact it should have been correctly accepted as a useful syringe.

Pre-fill accepted correctly, post-fill rejected incorrectly. The fourth problem could be that the pre-filled lubricated syringe could have been accepted correctly. If there is a post-fill quality test, the post-filled lubricated syringe could have been accepted incorrectly, by testing prior to the specified time post-fill quality test window, as in fact it should have been rejected. This syringe would have been incorrectly passed on to the patient as a useful syringe.

In alternate embodiment, the invention can be defined as a significant and crucial method and system improvement to the delivery of high-quality lubricant coatings being delivered along a syringe barrel's life. Especially, these improvements are not only significant in view of the current practice, but also these improvements could potentially be reducing health-risk or avoiding life-threatening situations. In view of this, embodiments of the invention could be defined as a quality control method or system for determining a lubricant coverage at the inside surface of a syringe barrel, wherein the significant and crucial improvement comprises either alone or in any combination of the following steps:

prior to filling the lubricant-covered barrel with an aqueous-based solution, obtaining one or more pre-fill optical properties of the lubricant-covered barrel, where the one or more pre-fill optical properties are obtained at a time $T_e$ defined as $T_{e,0} < T_e \leq T_{e,1}$, where $T_{e,0}$ is the time of the applying the lubricant, wherein $T_{e,1} = 0.051\eta$ defined in minutes, where η is a viscosity of the applied lubricant and defined in cSt, and where the one or more pre-fill optical properties are obtain using a first imaging system, and determining a pre-fill quality measure for the lubricant-covered barrel using the one or more pre-fill optical properties as input to a computer-implemented pre-fill barrel quality measure determination program executed on a first computer, where the pre-fill quality measure is used by a first syringe processing system to reject or accept the lubricant-covered barrel based on a predetermined pre-fill quality threshold.

post filling the syringe barrel with an aqueous-based solution, obtaining one or more post-fill optical properties of the filled lubricant-covered syringe barrel, where the one or more post-fill optical properties are obtained at a time $T_f$ defined as $T_f \geq T_{f,1}$, where $T_{f,1} = 8.8 \exp(0.0063\eta)$ defined in minutes and defined from $T_{f,0}$, where η is the viscosity of the applied lubricant and defined in cSt, where $T_{f,0}$ is the time of the filling the aqueous-based solution, and where the one or more post-fill optical properties are obtained using the first imaging system or a second imaging system, and determining a post-fill quality measure for the filled lubricant-covered barrel using the one or more post-fill optical properties as input to a computer-implemented post-fill barrel quality measure determination program executed on the first computer or a second computer, where the post-fill quality measure is used by the first syringe processing system or a second syringe processing system to reject or accept the filled lubricant-covered barrel based on a predetermined post-fill quality threshold.

Appendix

Syringe

A medical syringe 1800 is a pump with of a plunger 1810 that fits tightly in a cylindrical glass or plastic tube (called a barrel) 1820. Plunger 1810 can be pushed (arrow 1830) along inside cylindrical tube 1820, allowing the syringe to eject material from the end of the tube 1840. The open end 1842 of the syringe may be fitted with a hypodermic needle, a nozzle, or tubing 1840 to direct the flow of the material out of the barrel.

Lubricant Application

The application of the lubricant using a lubricant covering system is in accordance to Chan et al. (Syringe Siliconization Process Investigation and Optimization. J. Pharm. Sci. and Tech. 2012, 66 136-150). The syringe barrels in the examples in this invention are sprayed with Dow Corning oil, with a viscosity of 20 centistokes (cSt) and in some embodiments 1000 cSt. The volume sprayed was 0.5 μL with a flow rate of 2.5 slm (standard liter per minute) and nozzle temperature of 65 degrees Celsius. The spray system started dispensing the oil at 30 mm outside of the syringe barrel and stopped at 40 mm inside the syringe barrel. The duration of the spray process is 1 second. After the spray process, the syringe barrel is inspected using an imaging system.

Imaging

The imaging system 1900 image syringe barrel 1910 works together with a backlight 1920, paired with a light mask 1930 and a camera 1940. The purpose of mask 1930 is to produce a light pattern 1960 with alternating dark and light regions, which makes it easier to detect changes in the refractive index caused by the coalescing lubricant. An example of a light source that could be employed is a model LED light source. The lens that could be used is a Telecentric Lens with magnification. The camera could be a metal-oxide-semiconductor (CMOS or CCD). To capture images an exposure time of 2 milliseconds could be used.

What is claimed is:

1. A quality control method for determining a lubricant coverage at the inside surface of a syringe barrel for a pre-filled and post-filled syringe barrel, wherein the pre-filled syringe barrel is defined as prior/pre to a time of filling of the syringe barrel with an aqueous-based solution, and wherein the post-filled syringe barrel is defined as after/post a time of the filling of the syringe barrel with an aqueous-based solution, comprising:

for the pre-filled syringe barrel:
 (a) providing a pre-filled syringe barrel having an inner surface, wherein the inner surface has not yet been covered with a lubricant;
 (b) applying a lubricant to cover to the inner surface of the pre-filled syringe barrel using a lubricant covering device, therewith creating a lubricant-covered pre-filled syringe barrel;
 (c) prior to filling the lubricant-covered pre-filled syringe barrel with an aqueous-based solution, obtaining one or more pre-fill optical properties of the lubricant-covered barrel, wherein the one or more pre-fill optical properties are obtained at a time $T_e$ defined as $$T_{e,0} < T_e \leq T_{e,1}$$

wherein $T_{e,0}$ is the time of the applying the lubricant, wherein $$T_{e,1} = 0.05\eta$$

defined in minutes, wherein η is a viscosity of the applied lubricant and defined in cSt, and wherein the one or more pre-fill optical properties are obtained using a first imaging system;
 (d) determining a pre-fill quality measure for the lubricant-covered pre-filled syringe barrel using the one or more pre-fill optical properties as input to a computer-implemented pre-fill barrel quality measure determination program executed on a first computer, wherein the pre-fill quality measure is used by a first syringe processing system to reject or accept the lubricant-covered pre-filled syringe barrel based on a predetermined pre-fill quality threshold; and for the post-filled syringe barrel:
 (e) providing a pre-filled lubricant-covered syringe barrel, wherein the pre-filled lubricant-covered syringe barrel has not yet been filled with the aqueous-based solution;
 (f) filling the pre-filled lubricant-covered syringe barrel with an aqueous-based solution using an aqueous-based solution filling device, therewith creating a lubricant-covered post-filled syringe barrel;
 (g) obtaining one or more post-fill optical properties of the lubricant-covered post-filled syringe barrel, wherein the one or more post-fill optical properties are obtained at a time $T_f$ defined as $$T_f \geq T_{f,1},$$

wherein $$T_{f,1} = 8.8 \exp(0.0063\eta)$$

defined in minutes and defined from $T_{f,0}$, where η is the viscosity of the applied lubricant and defined in cSt, wherein $T_{f,0}$ is the time of the filling the aqueous-based solution, and wherein the one or more post-fill optical properties are obtained using the first imaging system or a second imaging system; and
 (h) determining a post-fill quality measure for the lubricant-covered post-filled syringe barrel using the one or more post-fill optical properties as input to a computer-implemented post-fill barrel quality measure determination program executed on the first computer or a second computer, wherein the post-fill quality measure is used by the first syringe processing system or a second syringe processing system to reject or accept the post-filled lubricant-covered barrel based on a predetermined post-fill quality threshold.

2. The quality control method as set forth in claim 1, wherein the one or more pre-fill optical properties and the one or more post-fill optical properties are optical changes related to the applied lubricant, changes in refractive index or optical features of the lubricant.

3. The quality control method as set forth in claim 1, wherein the aqueous-based solution is an aqueous-based drug-containing solution.

4. A quality control system for determining a lubricant coverage at the inside surface of a syringe barrel for a pre-filled and post-filled syringe barrel, wherein the pre-filled syringe barrel is defined as prior/pre to a time of filling of the syringe barrel with an aqueous-based solution, and wherein the post-filled syringe barrel is defined as after/post a time of the filling of the syringe barrel with an aqueous-based solution, comprising:

a pre-fill syringe barrel quality testing sub-system with:

(a) a lubricant covering device for applying a lubricant to cover an inner surface of the pre-filled syringe barrel, therewith creating a lubricant-covered pre-filled syringe barrel;

(b) a first imaging system for obtaining one or more pre-fill optical properties of the lubricant-covered pre-filled syringe barrel, prior to filling the lubricant-covered pre-filled syringe barrel with an aqueous-based solution, wherein the one or more pre-fill optical properties are obtained at a time $T_e$ defined as $$T_{e,0} < T_e \leq T_{e,1}$$

wherein $T_{e,0}$ is the time of the applying the lubricant, wherein $$T_{e,1} = 0.05\eta$$

defined in minutes, and wherein $\eta$ is a viscosity of the applied lubricant and defined in cSt;

(c) a computer-implemented pre-fill barrel quality measure determination program executed on a first computer for determining a pre-fill quality measure for the lubricant-covered pre-filled syringe barrel using the one or more pre-fill optical properties as input;

d) a first syringe processing system configured for rejecting or accepting the lubricant-covered pre-filled syringe barrel based on a predetermined pre-fill quality threshold and the pre-fill quality measure; and a post-fill syringe barrel quality testing sub-system with:

(e) an aqueous-based solution filling device for filling the lubricant-covered pre-filled syringe barrel with an aqueous-based solution, therewith creating a lubricant-covered post-filled syringe barrel;

(f) the first imaging system or a second imaging system for obtaining one or more post-fill optical properties of the lubricant-covered post-filled syringe barrel, wherein the one or more post-fill optical properties are obtained at a time $T_f$ defined as $$T_f \geq T_{f,1},$$

wherein $$T_{f,1} = 8.8 \exp(0.0063\eta)$$

defined in minutes and defined from $T_{f,0}$, where $\eta$ is the viscosity of the applied lubricant and defined in cSt, and wherein $T_{f,0}$ is the time of the filling the aqueous-based solution; and (g) a computer-implemented post-fill barrel quality measure determination program executed on the first computer or a second computer for determining a post-fill quality measure for the lubricant-covered post-filled syringe barrel using the one or more post-fill optical properties as input; and (h) the first syringe processing system or a second syringe processing system configured for rejecting or accepting the lubricant-covered post-filled syringe barrel based on a predetermined post-fill quality threshold and the post-fill quality measure.

5. The quality control system as set forth in claim 4, wherein the one or more pre-fill optical properties and the one or more post-fill optical properties are optical changes related to the applied lubricant, changes in refractive index or optical features of the lubricant.

6. The quality control system as set forth in claim 4, wherein the aqueous-based solution is an aqueous-based drug-containing solution.

* * * * *